(12) United States Patent
Bruce et al.

(10) Patent No.: US 8,359,179 B2
(45) Date of Patent: Jan. 22, 2013

(54) TEST EQUIPMENT AND PORTABLE TEST DEVICE

(75) Inventors: Peter George Bruce, Angus (GB);
Alasdair McCall Christie, Angus (GB);
Stephen Ferrier, Angus (GB);
Christopher Longbottom, Angus (GB);
Nigel Berry Pitts, Angus (GB)

(73) Assignee: 3D Diagnostic Imaging PLC, Douglas (IM)

( * ) Notice: Subject to any disclaimer, the term of this patent is extended or adjusted under 35 U.S.C. 154(b) by 1860 days.

(21) Appl. No.: 10/503,819

(22) PCT Filed: Feb. 8, 2003
(Under 37 CFR 1.47)

(86) PCT No.: PCT/GB03/00553
§ 371 (c)(1),
(2), (4) Date: Apr. 14, 2006

(87) PCT Pub. No.: WO03/065890
PCT Pub. Date: Aug. 14, 2003

(65) Prior Publication Data
US 2008/0097712 A1    Apr. 24, 2008

(30) Foreign Application Priority Data

| Feb. 8, 2002 | (GB) | .................................. 0202950.2 |
| Feb. 8, 2002 | (GB) | .................................. 0202966.8 |
| Feb. 8, 2002 | (GB) | .................................. 0202968.4 |
| Feb. 8, 2002 | (GB) | .................................. 0202977.5 |
| Sep. 16, 2002 | (GB) | .................................. 0221359.3 |
| Sep. 16, 2002 | (GB) | .................................. 0221360.1 |
| Sep. 16, 2002 | (GB) | .................................. 0221361.9 |
| Sep. 16, 2002 | (GB) | .................................. 0221362.7 |

(51) Int. Cl.
*G01R 15/00* (2006.01)

(52) U.S. Cl. .......................................... 702/108; 433/27
(58) Field of Classification Search ................. 702/108, 702/124, 112, 57, 71–77; 433/27, 72, 224
See application file for complete search history.

(56) References Cited

U.S. PATENT DOCUMENTS 3,782,366 A    1/1974    Brown
(Continued)

FOREIGN PATENT DOCUMENTS

DE    3 347 516 A    7/1985
(Continued)

OTHER PUBLICATIONS

GB Application No. 02 21 362.7; United Kingdom Search Report; Nov. 11, 2002.

(Continued)

*Primary Examiner* — Jonathan C Teixeira Moffat
*Assistant Examiner* — Hien Vo
(74) *Attorney, Agent, or Firm* — Sughrue Mion, PLLC

(57) ABSTRACT

The present invention relates to an equipment, device (10; 110) and apparatus for applying electrical stimuli to a system and acquiring a system response. According to the present invention there is provided a test equipment such as a portable test device (10; 110) for testing a system, the equipment comprising: signal generation means, signal receiving means, and signal processing means, wherein, in use, the signal generation means generates a signal to be applied to a system to be tested and the signal receiving means receives a response signal of the system, and the generated and response signals undergo processing by the signal processing means so as to provide a measure of a characteristic of the system, wherein further the generated signal comprises a plurality of periodic signals each of different frequency and phase and which are applied to the system simultaneously. The equipment finds particular use in the field of dentistry, but also finds other uses, e.g. in medicine and also in corrosion detection and battery testing.

31 Claims, 27 Drawing Sheets

U.S. PATENT DOCUMENTS

| | | | |
|---|---|---|---|
| 3,841,311 A | 10/1974 | Brown | |
| 4,164,214 A | 8/1979 | Stark et al. | |
| 4,193,408 A | 3/1980 | Fujino | |
| 4,537,573 A | 8/1985 | Sunada | |
| 4,991,128 A | 2/1991 | Evans et al. | |
| 5,333,618 A | 8/1994 | Lekhtman et al. | |
| 5,490,520 A * | 2/1996 | Schaefer et al. | 128/848 |
| 5,759,159 A * | 6/1998 | Masreliez | 600/547 |
| 5,870,699 A | 2/1999 | Canada et al. | |
| 5,952,803 A | 9/1999 | Canada et al. | |
| 5,956,658 A | 9/1999 | McMahon | |
| 5,965,819 A | 10/1999 | Piety et al. | |
| 6,054,038 A | 4/2000 | Davis et al. | |
| 6,078,874 A | 6/2000 | Piety et al. | |
| 6,111,738 A | 8/2000 | McGoogan | |
| 6,266,995 B1 * | 7/2001 | Scott | 73/23.2 |
| 6,312,392 B1 | 11/2001 | Herzon | |
| 6,313,646 B1 | 11/2001 | Davis et al. | |
| 6,328,878 B1 | 12/2001 | Davis et al. | |
| 6,502,046 B1 * | 12/2002 | Yoon et al. | 702/76 |
| 6,954,668 B1 * | 10/2005 | Cuozzo | 607/2 |
| 2007/0182367 A1 * | 8/2007 | Partovi | 320/108 |

FOREIGN PATENT DOCUMENTS

| | | |
|---|---|---|
| DE | 10 006598 A | 8/2001 |
| EP | 0 332 131 A2 | 9/1989 |
| EP | 0 446 874 A2 | 9/1991 |
| GB | 2 331 585 A | 5/1999 |
| GB | 2 334 586 A | 8/1999 |
| JP | 09-271276 A | 10/1997 |
| JP | 10-179536 A | 7/1998 |
| JP | 11-128197 A | 5/1999 |
| WO | WO 97/42909 | 11/1997 |
| WO | WO 98/12983 | 4/1998 |
| WO | WO 98 12983 A | 4/1998 |
| WO | WO 99/01754 A1 | 1/1999 |
| WO | WO 01 27605 A | 4/2001 |
| WO | WO 01/27605 A1 | 4/2001 |

OTHER PUBLICATIONS

GB Application No. 02 21 361.9; United Kingdom Search Report; Oct. 29, 2002.

GB Application No. 02 21 359.3; United Kingdom Search Report; Oct. 31, 2002.

GB Application No. 02 21 360.1; United Kingdom Search Report; Nov. 7, 2002.

"ES18 Electrochemical Corrosion Test System"; AC—Impedance Test System Software Manual; *PCI automation Embeded Computer Systems Inc.*; cover and pages pp. 2-54 followed by 4 attachment sheets.

Malcolm Levinkind B.D.S; "Impedance Spectroscopy of Human Enamel and Dentine Relating to their Physical Structure and Equivalent Circuits"; Jun. 1992; *Department of Child Dental Health The London Hospital Medical College*; (7 pages).

* cited by examiner

| PIN | FUNCTION (CH1)      | PIN | FUNCTION (CH2)      |
|-----|---------------------|-----|---------------------|
| 1   | ANALOGUE OUT (CH Z) | 1   | ANALOGUE IN (CH Y)  |
| 2   | EXT TTL TRIGGER     | 2   | ANALOGUE IN (CH X)  |
| 3   |                     | 3   |                     |
| 4   | DGND                | 4   |                     |
| 5   | AGND                | 5   | AGND                |
| 6   |                     | 6   |                     |

| PIN | FUNCTION (POWER) | PIN | FUNCTION (RS232) |
|-----|------------------|-----|------------------|
| 1   | EXT DC IN        | 1   |                  |
| 2   |                  | 2   | TxD OUT          |
| 3   |                  | 3   | RxD IN           |
| 4   | DGND             | 4   | DTR OUT          |
| 5   |                  | 5   | DGND             |
| 6   |                  | 6   | DCD/DSR          |
| 7   |                  | 7   | CTS IN           |
|     |                  | 8   | RTS OUT          |

| PIN | FUNCTION | |
|---|---|---|
| 1 | RS232 DTR | connect pin 1 to pin 6 |
| 2 | ANALOGUE IN (CH Y) | |
| 3 | ANALOGUE OUT (CH Z) | |
| 4 | EXT TTL TRIGGER | |
| 5 | AGND | |
| 6 | RS232 DCD/DSR | |
| 7 | RS232 TxD OUT | |
| 8 | RS232 RxD IN | |
| 9 | RS232 CTS IN | |
| 10 | RS232 RTS OUT | |
| 11 | EXT DC IN | |
| 12 | DGND | |

*Signal Cable*

*RS-232 cable*

*Power Cable*

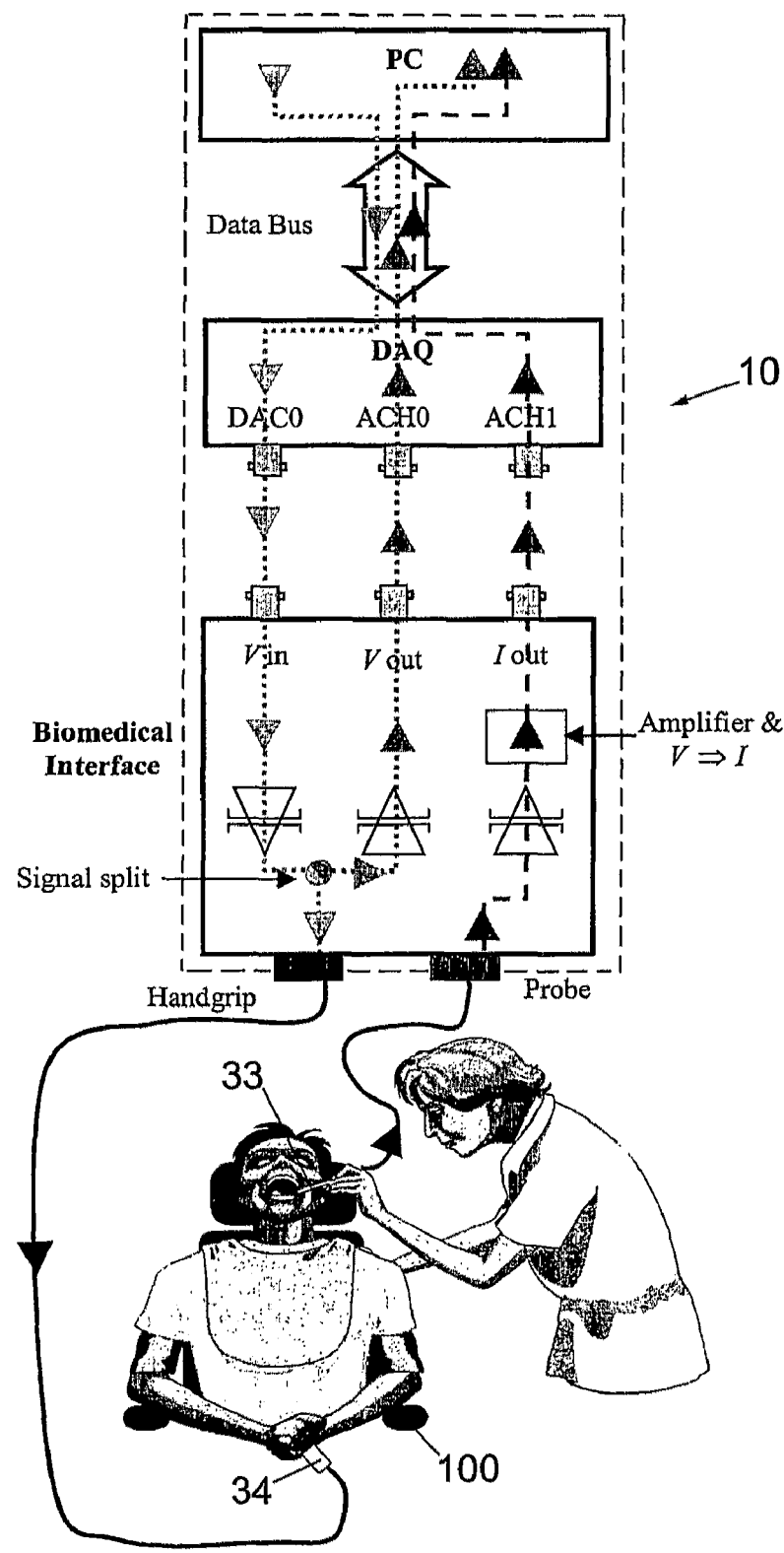
ACIST full signal path    Fig. 18(b)

Fig. 20a
Fig. 20b
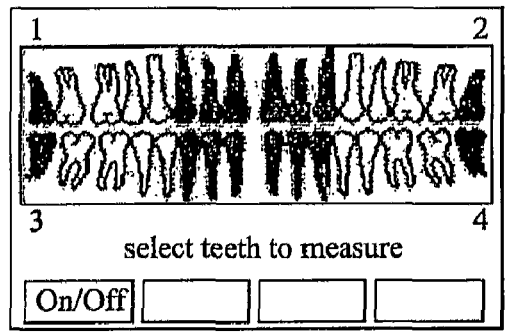
Fig. 20c
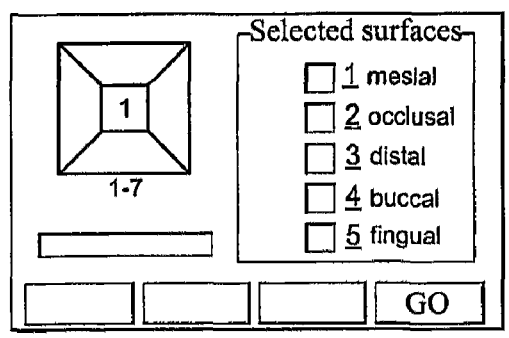
Fig. 20d

TEST EQUIPMENT AND PORTABLE TEST DEVICE

This application claims the benefit of the earlier filing date of GB 02 02 977.5, filed 8 Feb. 2002; GB 02 02 950.2, filed 8 Feb. 2002; GB 02 02 966.8, filed 8 Feb. 2002; GB 02 02 968.4, filed 8 Feb. 2002; GB 02 21 362.7, filed 16 Sep. 2002; GB 02 21 361.9, filed 16 Sep. 2002; GB 02 21 359.3, filed 16 Sep. 2002; and GB 02 21 360.1; filed 16 Sep. 2002, which are hereby incorporated by reference in the entirety.

FIELD OF INVENTION

The present invention relates to an equipment and to a device and apparatus for applying electrical stimuli to a system and acquiring a system response.

The invention particularly, though not exclusively, relates to an equipment, device and apparatus for use in detecting dental 'caries', ie dental decay or caries or 'carious lesions', by electrical means.

The invention also particularly, though not exclusively, relates to an equipment, device and apparatus for use in a clinical/medical environment.

The equipment, device and apparatus may also find use in other non-clinical technical fields.

BACKGROUND TO INVENTION

Many physical or chemical phenomena give rise to a specific electrical response on application of an electrical stimulus. Consequently, such measurements are widely used in a variety of laboratory and industrial environments.

The application of these measurements may use AC or DC based methods such as potential steps, voltammetry and electrochemical impedance spectroscopy (EIS), also known by the present inventors as the AC impedance spectroscopy technique (ACIST™). EIS has become particularly useful in the investigations of charge transfer, ion transport and adsorption processes, among others. In addition, impedance measurements have little or no effect on the sample under investigation making it applicable where changes in the measured system due to the effect of electrical polarisation are undesirable, and thus particularly suitable for non-destructive testing and material characterisation in general.

Measurements of impedance spectra can be made using one of two methods, that is, the frequency domain or the time domain. In the frequency domain impedance measurements made using, for example, the EIS technique can be performed using a single sine method. With the single sine technique, a small amplitude fixed frequency sinusoidal signal is applied to the system under study, and the response signal is measured. In this frequency domain the in-phase (real) and out-of-phase (imaginary) components of the total impedance are determined. From this information, the phase shift between source and response waveforms is calculated which defines the magnitude of the impedance. To construct an impedance spectrum, the single sine technique requires a number of measurements to be performed at discrete frequencies in a sequential manner.

In some studies in which the measurements are performed in the frequency domain, the impedance spectra are achieved by analysis of the response of a test system to an applied signal of single frequency and then repeating the process at different frequencies to achieve the desired frequency range. This technique has become colloquially known as the "swept sine technique" whereby a single frequency signal is applied to the test system and the response analysed and recorded, the process then being repeated for signals of different frequency and by this means an impedance spectrum is built up.

The equipment which is used to perform measurements in the frequency domain, as described above, is typically a computer controlled Frequency Response Analyser (FRA) attached to an electrochemical interface to measure current or voltage response. An example of such a swept sine arrangement is shown in FIG. 1. This equipment which is used to measure AC impedance in the frequency domain, comprises a frequency response analyser (FRA), in this case a Solartron 1255, an electrochemical interface (ECI), in this case a Solartron 1286, a PC with general-purpose interface bus (GPIB) and controller software which links all of these devices. In such an arrangement of equipment, the FRA generates and measures AC signals and the ECI operates as a potentiostat/galvanostat; however it may simply be used as a current measuring resistor and amplifier. Both applied signals and response signals would be returned to input channels of the FRA and subsequently acquired by the PC via the interface board for further data manipulation.

Similar equipment exists for measurements in the time domain such as Stanford Research Systems SR780. However, for these measurements the equipment typically comprises a spectrum/network analyser, a PC with GPIB and controller software linking each of these devices.

As can be seen, such equipment is usually heavy and expensive. These types of equipment arrangements also require mains power therefore making them unsuitable for use with human subjects without the provision of isolation apparatus. Additionally, complex software is required to be installed in each equipment arrangement to link the component devices and perform the required processing functions. Further, due to its cumbersome nature the usefulness of known conventional apparatus is limited in some circumstances. In particular, known apparatus is unable to be easily used in small or awkward spaces, nor is known apparatus convenient for performing measurements in environments outside of the laboratory as this would require the disassembly and moving of the components of the testing apparatus and the reassembly in the testing environment.

Caries is defined as the progressive decay of tooth or bone, and dental caries is the most common ailment known worldwide. Dental caries can be treated by either removing the decayed material in the tooth and filling the resultant space with a dental amalgam, or in severe cases, by removal of the entire tooth.

The early diagnosis of dental caries is of utmost importance to any subsequent treatment since by the time pain is felt due to decay of the tooth, the treatment required to restore the tooth may be extensive, and in some cases, the tooth may be lost.

Historically, the diagnosis of dental caries has been primarily visual, frequently accompanied by tactile examination using a mechanical probe or radiographic examination. A patient may also seek an examination by a dental surgeon when in pain. This symptom itself is often not a reliable indicator of the presence of caries and the surgeon must identify the offending tooth by visual examination and/or by the use of a mechanical probe.

Caries is often at an advanced stage by the time diagnosis is made using conventional examinations or when it gives rise to symptoms. This may reduce options available for treatment.

The diagnosis of caries by conventional techniques has become increasingly difficult. This is a result of several factors, including apparent changes in the morphology and in the rate of progress and distribution of carious lesions, as well as the inaccessibility of approximal (mutually contacting) dental surfaces and the complicated anatomy of pit and fissure sites on the occlusal (biting) surfaces.

In response to these generally unsatisfactory and unreliable methods of diagnosis attempts have been made to develop electrical/electronic means for the diagnosis of caries.

Electrical Caries Detectors (ECD's) generally comprise a probe having a first (probe) electrode which is placed in contact with the tooth to be tested, and a second (counter) electrode separate from the probe which is placed in contact with another part of the body of the patient in order to complete an electrical circuit connecting the two electrodes. The second electrode may be held by the patient or may be placed in contact against the gingiva (gum) or oral mucosa (inside cheek). An alternating electric current of fixed frequency is passed through the tooth and the resistance to this is measured. This electrical resistance has been found to correlate approximately inversely with the extent of caries in the tooth. The technique may involve measurement at a single point on the surface of the tooth, or the use of an electrically conductive paste, providing a measurement for the surface as a whole. Known ECD's suffer from a number of problems, eg as mentioned hereinbefore.

WO 98/12983 (ORMCO CORPORATION) discloses an apical detection apparatus, comprising: a first electrode, the first electrode including a conductive probe shaped for penetrating a root canal of a tooth; a second electrode configured to electrically contact a patient's body; a phase detector coupled to the first and second electrodes, the phase detector being operative to detect a phase of a complex impedance having a real component and a reactive component; and a user interface coupled to the phase detector to provide an indication to a user of a parameter that is a function of the detected phase.

WO 97/42909 (UNIVERSITY OF DUNDEE) discloses a method for use in the detection of dental caries, comprising the steps of placing: at least one probe electrode in electrical contact with a surface of a patient's tooth, placing a second electrode in electrical contact with another part of the body of the patient, passing an alternating electrical current between said probe and second electrodes, and measuring the electrical impedance between the electrodes to said electrical current; wherein the frequency of said alternating current is sequentially varied over a predetermined frequency range and the electrical impedance is measured for a plurality of frequency values within said range.

An object of at least one embodiment of at least one aspect of the present invention is to obviate or mitigate at least one of the aforementioned problems/disadvantages.

It is also an object of the at least one embodiment of at least one aspect of the present invention to provide a dedicated test equipment or portable test device providing signal generation means, signal receiving means and signal processing means beneficially within a unitary body or within a single casing or enclosure or alternatively in a modular form which is advantageously readily assembled and disassembled.

It is further an object of at least one embodiment of at least one aspect of the present invention to provide a test equipment or device which generates a signal and receives a response signal in the time domain and analyses said signals in the frequency domain, ie measures in the time domain and analyses in the frequency domain.

It is a yet further object of at least one embodiment of at least one aspect of the present invention to provide a test equipment or portable test device capable of testing a whole tooth in vivo, and in a time frame acceptable to clinician and/or patient, eg in less than 10 to 15 seconds, and preferably in less than 1 to 3 seconds.

SUMMARY OF INVENTION

Device

According to a first aspect of the present invention, there is provided a test equipment, the equipment comprising:
signal generation means,
signal receiving means, and
signal processing means,
wherein, in use, the signal generation means generates an electrical signal to be applied to a system to be tested and the signal receiving means receives a response electrical signal of or from the system, and the generated and response signals undergo processing by the signal processing means so as to provide a measure of a characteristic of the system, wherein further the generated signal comprises a plurality of periodic signals each of different frequency and preferably different phase and which are applied to the system simultaneously.

The generated signal may be termed a "complex signal".

In use, the generated signal may be constructed from a plurality of periodic signals which can be deconstructed for analysis.

The response signal may be deconstructed into a plurality of periodic signals for analysis.

In an alternative the generated signal may comprise a white noise signal, which may be deconstructed into a plurality of periodic signals.

The characteristic of the system may comprise an AC determined characteristic such as imminence, eg preferably impedance or alternatively admittance, permittivity or electric modulus.

Preferably the signal generation means comprises a signal assembly unit, which is controllable by software, e.g. embedded software, and operates at least in one mode according to an algorithm:

$$E_k = a_o \sum_{i=1}^{n} \sin(2\pi i f_0 t_k + \theta_i)$$

where $E_k$=voltage at any given time $t_k$,
$\theta_i$=phase randomised for each periodic signal.
so as to provide the plurality of periodic output signals.

Preferably each of the plurality of periodic signals comprises a sine wave.

Preferably the signal processing means performs a Fast Fourier Transform (FFT) analysis on the generated and response signals.

Preferably the phase of each of the plurality of periodic signals generated by the signal generation means is random.

Preferably one of the periodic signals has a frequency $f_o$, and each other periodic signal has a frequency which is a multiple of frequency $f_o$.

Preferably the generated signal is applied to the system for a period of time comprising at least $1/f_o$ or a multiple of $1/f_o$.

Preferably each point k of the generated signal is given by:

$$E_k = a_o \sum_{i=1}^{n} \sin(2\pi i f_0 t_k + \theta_i)$$

where $E_k$=voltage at any given time $t_k$,
$\theta_i$=phase randomised for each periodic signal.

Preferably there may be provided means to control the signal generation means.

Preferably the means to control the signal generation means may allow a user to select, switch or program the signal generation means to operate in a different mode to generate a different electrical signal(s), e.g. a single signal, e.g. a DC signal or periodic signal such as a single sine wave or swept sine wave.

Advantageously the test equipment is portable, eg capable of being carried by hand or hand held.

In one most preferred embodiment the test equipment is in the form of a portable test device wherein the signal generation means, signal receiving means and signal processing means are provided within a common/single/unitary enclosure, casing or module. Such a device is therefore "self-contained".

In an alternative embodiment the test equipment comprises a computer means optionally including the signal processing means and a module preferably including the signal generation means and/or the signal receiving means, the computer means and the module being separate/separable one from the other.

In the latter case there may also be provided an isolation unit to electrically isolate the system from the module and/or computer means, in use. This is particularly required for dental and medical uses if the computer means and/or separate module are mains powered.

Preferably there are provided means for electrically connecting or electrically docking the computer means and the separate module one to the other.

The computer means may comprise a notebook or laptop PC.

According to a second aspect of the present invention there is provided a test apparatus such as a portable test apparatus for testing a system, the apparatus comprising:

a test equipment according to the first aspect of the present invention;

electrode means which are, in use, applied to the system so as to apply the generated signal to the system and receive the response signal from the system.

The electrode means are preferably applied to the system in a non-invasive and non-destructive manner.

According to a third aspect of the present invention there is provided a portable test device for generating an electrical signal to be applied to a system to be tested and acquiring a response signal generated by the system, the device comprising:

signal generation means, signal receiving means, and signal processing means, wherein, in use, the device generates a signal to be applied to a system to be tested and receives a response signal of the system which was tested whereby the applied and received signals undergo processing by the signal processing means to provide data.

The data may be indicative of a system characteristic.

The device may also comprise data storage means to which the data is transferred for storage.

Preferably the device may be hand held.

Preferably the device includes means for visually displaying data.

Preferably the device measures an impedance of the system.

Preferably the device is battery operated.

Preferably the device may include means for associating the device with electrode means comprising at least a first electrode and a second electrode wherein the first electrode applies the generated signal(s) to the system to be tested and the second electrode collates response signal(s) from the system.

Conveniently the device may comprise means by which the device may be connected to a mains power supply to allow charging of the battery(ies) to take place.

Preferably the device is configured or arranged such that connection to an external power supply and electrode means cannot occur simultaneously.

Alternatively the device is configured or arranged such that connection to an external power supply and electrode means can occur simultaneously.

Conveniently the device is provided with safety features conforming to appropriate standard requirements for medical/dental electrical equipment.

Preferably the device may be provided with only one input/output port wherein the device cannot be connected to an external power supply and a system to be tested simultaneously.

Alternatively the device may be provided with two or more input/output ports wherein power to the device and the signals transferring to and from the device are assigned to individual input/output ports.

The signal applied to the system may comprise at least one period of a periodic signal such as an AC signal.

Preferably the applied signal is formed of a plurality of periodic waves.

Conveniently each of the periodic waves is of a different frequency and random phase.

Preferably each of the waves is a sine wave.

Alternatively the applied signal is a square wave or other waveform, eg triangle, saw tooth or arbitrary.

Alternatively the applied signal may be of a single frequency. The equipment may also be selected to operate in a swept sine mode.

Preferably the means for analysing the applied signal and received signal performs Fast Fourier Transform (FFT) spectrum analysis upon the applied signal and received signal.

Preferably the signal receiving means includes data acquisition means.

Preferably the device may be adapted for use detecting a dental or medical condition in vivo in a system comprising at least in part biological materials or tissues eg at least part of a human or animal body.

Conveniently the device may be adapted for use detecting a dental or medical condition in vitro in a system comprising at least in part biological materials or tissues, eg at least part of a human or animal body.

Alternatively the device may be adapted for use with a system such as a battery, fuel cell or the like.

Preferably tests carried out using the device generating a signal having a frequency in the range of DC-100 kHz provides accurate results for measurements made involving systems characterised by low frequency response such as polymers, dielectrics, electrode processes or other high impedance media.

Preferably tests performed using the device generating a signal in a range above 100 kHz provides accurate results for measurements made involving systems characterised by high frequency response such as highly conducting electrolytes or other low impedance media.

Conveniently the device may be adapted for use in detecting corrosion or the condition of coatings such as paints and polymers using non-destructive testing techniques.

Preferably the device is adapted or customised for specific end-use by embedded PC-based control software.

Conveniently the device may be programmed to perform a range of measurements with subsequent analysis, presentation, data storage and/or retrieval.

Preferably the device further comprises means for performing variable amplification on the received signal.

According to a fourth aspect of the present invention there is provided a portable apparatus for applying electrical stimulus to a system and acquiring a system response, the apparatus comprising:
  signal generation means,
  signal receiving means,
  signal processing means, and
  electrode means which are, in use, applied to the system, wherein a generated signal is applied to the system by said electrode means, a response signal of the system is detected by said electrode means and received by the signal receiving means, and the applied and received signals undergo processing by the signal processing means.

Preferably data generated by the signal processing means is transferred to data storage means for storage.

Preferably the signal processing means performs signal analysis on the generated or applied signal and response or received signal.

Conveniently the electrode means comprises one or more electrodes and may comprise an array of electrodes.

According to a fifth aspect of the present invention there is provided a portable device for generating an electrical signal to be applied to a system and acquiring a response signal generated by the system, the portable device comprising:
  signal generation means,
  signal receiving means,
  signal processing means, and
  a single input/output electrical connection means wherein preferably the electrical connection means comprises a customised multi-pin plug port which is configured such that each pin is assigned a function so that a plurality of operations may be performed by the device via the port.

Preferably the device may further comprise data storage means.

Preferably the plurality of operations performed by the device via the port or single input/output electrical connection means include at least one of charging a battery of the device, transferring signals or data into the device, transferring signals or data out of the device.

Conveniently the port is a (customised)12-way port commercial socket.

According to a sixth aspect of the present invention there is provided a portable device for generating an electrical signal to be applied to a system and acquiring a response signal generated by the system, the portable device comprising:
  signal generation means,
  signal receiving means,
  signal processing means, and
  selection means,
  wherein the selection means are used to select an appropriate signal to be generated, the device generates a function to be performed by the device and the appropriate signal to be applied to a system to be tested, and receives a response signal of the system which was tested whereby the applied and received signals undergo processing by the signal processing means to provide data.

Preferably the data provided is transferred to data storage means for storage.

Preferably the device includes means for visually displaying data.

Preferably the selection means may also be used to select processing steps to be performed by the signal processing means.

Preferably the function of the device selected is such that the device performs electrochemical measurements in the time domain.

Alternatively the function of the device may be selected such that the device performs electrochemical measurements in the frequency domain.

Preferably the generated signal is at least one AC signal.

Alternatively the generated signal is a DC signal.

According to a seventh aspect of the present invention there is provided a portable device for generating a complex electrical signal to be applied to a system and acquiring a response signal generated by the system, the portable device comprising:
  signal generation means,
  signal receiving means, and
  signal processing means,
  wherein the device generates a complex signal to be applied to a system to be tested and receives a response signal of the system which was tested whereby the applied and received signals undergo processing by the signal processing means to provide data indicative of a feature of the system.

Preferably the data provided is transferred to data storage means for storage.

According to an eighth aspect of the present invention there is provided a portable device for generating a sequence of predetermined electrical signals to be applied to a system and acquiring a corresponding sequence of response signals generated by the system, the portable device comprising:
  signal generation means,
  signal receiving means, and
  signal processing means,
  wherein the device generates a sequence of predetermined signals to be applied to a system to be tested, and receives a corresponding sequence of response signals of the system which was tested, whereby the applied and received signals undergo processing by the signal processing means to provide data indicative of a characteristic of the system.

Preferably the data provided is transferred to data storage means for data storage.

According to a ninth aspect of the present invention there is provided a portable device for detecting a dental condition by generating an electrical signal to be applied to a system and acquiring a response signal generated by the system, the portable device comprising:
  signal generation means,
  signal receiving means, and
  signal processing means,
  wherein, in use, the device generates a signal to be applied to a system to be tested, and receives a response signal of the system which was tested whereby the applied and received signals undergo processing by the signal processing means to provide data indicative of a characteristic of the system.

Preferably the provided data is transferred to data storage means for storage.

Preferably tests carried out using the device generating a signal(s) having a frequency(ies) in the range of 1 Hz-100 kHz provides accurate results for measurements made involving systems characterised by low frequency response such as high impedance media or dental hard tissue and, for example, abrasion, attrition, caries, erosion or corrosion thereof or indeed any change in the tissue by any means, e.g. mechanical or chemical.

Herein the term "caries" includes at least chemical dissolution of dental tissues by bacterial degradation products, e.g. acids from low molecular weight sugars.

Further herein "erosion" includes at least loss of tooth substance by a chemical process that does not involve bacterial action. In other words, chemical dissolution of teeth by any other agent.

Herein further, "corrosion" includes at least oxidation or other changes of materials of fillings such as amalgam fillings e.g. including: silver (Ag); copper (Cu); zinc (Zn); tin (Sn) and/or mercury (Hg).

The device may therefore find use in detection and/or measurement of primary or secondary caries or any other changes in natural or reconstructive dental materials.

It should be understood that the term "primary caries" includes an original carious lesion of a tooth and also should include all lesions not occurring adjacent to restorations, i.e. all non-secondary/non-recurrent caries. Furthermore the term "secondary caries" includes caries occurring adjacent to a restoration.

Preferably tests performed using the device generating a signal in a range above 100 kHz provides accurate results for measurements made involving systems characterised by high frequency response such as soft tissue or other low impedance media.

According to a tenth aspect of the present invention there is provided use in the detection of clinical conditions of a portable device for generating an electrical signal to be applied to the system and acquiring a response signal generated by the system, the portable device comprising:

signal generation means,
signal receiving means,
signal processing means, and
analogue circuitry, wherein the analogue circuitry includes medical safety features which allows the device to perform tests in in vivo environments wherein the device generates a signal to be applied to a system under test and receives a response signal of the system which was tested whereby the applied and received signals undergo processing by the signal processing means providing data indicative of a characteristic of the system.

Preferably the provided data is transferred to data storage means for storage.

Conveniently the safety features of the analogue circuitry conform to the appropriate Standard requirements for medical electrical equipment.

Preferably the device may be provided with only one input/output port wherein the device cannot be connected to an external power supply and a system to be tested simultaneously.

Preferably tests carried out using the device generating a signal(s) having a frequency(ies) in the range of 1 Hz-100 kHz provides accurate results for measurements made involving systems characterised by low frequency response such as bone or other hard tissue including detecting the corrosion or erosion thereof, or other high impedance media.

Preferably tests performed using the device generating a signal(s) in a range above 100 kHz provides results for measurements made involving systems characterised by high frequency response such as soft tissue or other low impedance media.

Herein, the device may be used in vivo to measure or monitor a state of material used in reconstruction of a body part, e.g. a prosthetic, or a metal or synthetic "pin" or the like, and for example the corrosion thereof.

According to an eleventh aspect of the present invention there is provided a portable device for generating an electrical signal to be applied to a system and acquiring a response signal generated by the system, the portable device comprising:

signal generation means,
signal receiving means,
signal processing means, and
electrode means comprising at least a first electrode and a second electrode, wherein the device generates a signal to be applied via the first electrode to a system to be tested, and receives via the second electrode a response signal of the system which was tested whereby the applied signal and received signal undergo processing by the signal processing means to provide data indicative of a characteristic of the system, the first and second electrode of the device having been selected for the application and receiving of the signals in a manner which provides (meaningful) data.

Preferably the data provided is transferred to data storage means for storage.

According to a twelfth aspect of the present invention there is provided a portable device for generating an electrical signal to be applied to the system and acquiring a response signal generated by the system, the portable device comprising:

signal generation means,
signal receiving means,
signal processing means, and
selection means, wherein the device generates the signal to be applied to the system to be tested and receives the response signal of the system which was tested whereby the applied and received signals undergo processing by the signal processing means to provide data indicative of a characteristic of the system, the selection means being used to determine the applied signal and ratio obtained by the device in order to compensate for noise.

Preferably the data provided is transferred to data storage means for storage.

Dental Uses

According to a first aspect of the present invention there is provided use of a test equipment such as a portable test equipment or device in the detection of dental states or conditions such as dental caries, the equipment comprising:

signal generation means,
signal receiving means, and
signal processing means, wherein, in use, the signal generation means generates an electrical signal to be applied to a tooth to be tested and the signal receiving means receives a response electrical signal of the tooth, and the generated and response signals undergo processing by the signal processing means so as to provide a measure of a characteristic of the tooth, wherein further the generated signal comprises a plurality of periodic signals each of different frequency and phase and which are applied to the tooth simultaneously.

The characteristic of the tooth may comprise an AC determined characteristic such as imittence, eg preferably impedance or alternatively admittance, permittivity or electric modulus.

Preferably the signal generation means comprises a signal assembly unit, which is software controllable, and operates at least in one mode according to an algorithm:

$$E_k = a_o \sum_{i=1}^{n} \sin(2\pi i f_0 t_k + \theta_i)$$

where $E_k$=voltage at any given time $t_k$, $\theta_i$=phase randomised for each periodic signal so as to provide the plurality of periodic output signals.

Preferably each of the plurality of periodic signals comprises a sine wave.

Preferably the signal processing means performs a Fast Fourier Transform (FFT) analysis on the generated and response signals.

Preferably the phase of each of the plurality of periodic signals generated by the signal generation means is random.

Preferably one of the periodic signals has a frequency $f_o$, and each other periodic signal has a frequency which is a multiple of frequency $f_o$.

Preferably the generated signal is applied to the tooth for a period of time comprising $1/f_o$ or a multiple of $1/f_o$. Preferably each point k of the generated signal is given by:

$$E_k = a_o \sum_{i=1}^{n} \sin(2\pi i f_0 t_k + \theta_i)$$

where $E_k$=voltage at any given time $t_k$, $\theta_i$=phase randomised for each periodic signal.

Preferably there may be provided means to control the signal generation means.

Preferably the means to control the signal generation means may allow a user to select, switch or program the signal generation means to operate in a different mode and generate a different electrical signal(s), eg a single signal, eg a DC signal or a periodic signal such as a single sine wave.

According to a second aspect of the present invention there is provided use of a test apparatus such as a portable test apparatus in the detection of dental states or conditions such as dental caries, the apparatus comprising:

a test equipment according to the first aspect of the present invention;

electrode means which, in use, are applied to the tooth and/or patient so as to apply the generated signal to a tooth and receive the response signal from the tooth.

The electrode means are preferably applied to the tooth in a non-invasive and non-destructive manner.

According to a third aspect of the present invention there is provided a method of detecting dental states or conditions such as dental caries comprising the steps of:

providing a test apparatus according to the second aspect of the present invention;

generating an electrical signal and applying said electrical signal to a tooth;

detecting a response electrical signal;

processing the generated and response signals so as to provide a measure of a characteristic of the tooth.

According to a fourth aspect of the present invention there is provided a dentist's chair or light unit providing or having detachably attached thereto a test equipment or device, the equipment or device comprising:

signal generation means,
signal receiving means, and
signal processing means, wherein, in use, the signal generation means generates an electrical signal to be applied to a tooth to be tested and the signal receiving means receives a response electrical signal of the tooth, and the generated and response signals undergo processing by the signal processing means so as to provide a measure of a characteristic of the tooth, wherein further the generated signal comprises a plurality of periodic signals each of different frequency and phase and which are applied to the tooth simultaneously.

According to a fifth aspect of the present invention there is provided use in the detection of dental conditions of a portable test device for generating an electrical signal to be applied to a system and acquiring a response signal generated by the system, the device comprising:

signal generation means,
signal receiving means, and
signal processing means, wherein, in use, the device generates a signal to be applied to a system to be tested and receives the response signal of the system which was tested whereby the applied and received signals undergo processing by the signal processing means providing data which may be indicative of a system characteristic.

The device may also comprise data storage means to which the data is transferred for storage.

Preferably the device may be hand held.

Preferably the device includes means for visually displaying data.

Preferably the device measures an impedance of the system.

Preferably the device is battery operated.

Conveniently the device may comprise means by which the device may be connected to a mains power supply to allow charging of the battery(ies) to take place.

Preferably the portable device may be associated with at least a first electrode and a second electrode wherein the first electrode applies the generated signal to the system to be tested and the second electrode collects response signal(s) from the system tested.

Most preferably the device includes means for ensuring connection to an external power supply and connection to electrode means cannot occur simultaneously.

Alternatively the device is configured or arranged such that connection to an external power supply and electrode means can occur simultaneously.

Conveniently the device is provided with safety features, eg conforming to the appropriate British standard requirements for medical electrical equipment.

Preferably the device may be provided with only one input/output port wherein the device cannot be connected to an external power supply and a system to be tested simultaneously.

Alternatively the device may be provided with two or more input/output ports wherein the power to the device and the signals transferring to and from the device are assigned to individual input/output ports.

Preferably the signal applied to the system comprises at least one period of a periodic signal such as an AC signal.

Preferably the applied signal is formed of a plurality of periodic waves.

Conveniently each of the periodic waves is of a different frequency and random phase.

Preferably each of the waves is a sine wave.

Alternatively the applied signal is of a single frequency.

Preferably the applied signal is a sine wave.

Alternatively the signal applied to the system is a DC signal.

Alternatively the applied signal is a square or other form e.g. triangle, saw tooth or arbitrary wave.

Preferably the means for analysing the applied signal and received signal performs Fast Fourier Transform (FFT) spectrum analysis upon the applied signal and received signal.

Preferably the signal receiving means includes data acquisition means.

Preferably the device may be used for detecting a dental condition in vivo.

Conveniently the device may be used for detecting a dental condition in vitro.

Preferably the device is adapted or customised for specific end-use by embedded PC-based control software.

Conveniently the device may be programmed to perform a range of measurements with subsequent analysis, presentation, data storage and/or retrieval.

Preferably the device further comprises means for performing variable amplification on the received signal.

According to a sixth aspect of the present invention there is provided a method for detecting a dental condition by generating an electrical signal for application to a system and receiving the response signal generated by the system tested using a portable device, the method comprising the steps of:
  generating a signal to be applied to a system;
  detecting a response signal generated by the said system;
  receiving said detected response signal;
  processing said applied signal and received signal;
  generating data indicative of a feature of the system from said processed signals;
  wherein the system tested is a dental system.

Preferably the method further comprises the step of storing the said generated data in a data storage means.

Conveniently the method includes the step of applying the generated signal to a system comprising at least one tooth in vivo.

Alternatively the method includes the step of applying the generated signal to a system comprising at least one tooth in vitro.

According to a seventh aspect of the present invention there is provided a portable apparatus for detecting a dental condition by applying electrical stimulus to a dental system and acquiring response of the dental system, the apparatus comprising:
  signal generation means,
  signal receiving means,
  signal processing means, and
  electrode means which are, in use, applied to the system,
  wherein a generated signal is applied to the system by said electrode means, a response signal of the system is detected by said electrode means and received by the signal receiving means, and the applied and received signals undergo processing by the signal processing means.

Preferably data generated by the signal processing means is transferred to data storage means for storage.

Preferably the signal processing means performs signal analysis on the generated signal and received signal.

Preferably the signal receiving means includes a data acquisition means.

Conveniently the electrode means comprises one or more electrodes and may comprise an array of electrodes.

Preferably the signal applied to the system is at least one AC signal.

According to an eighth aspect of the present invention there is provided a method of performing electrochemical impedance measurements on a dental system using a portable device, the method comprising the steps of:
  generating a signal;
  applying the generated signal to a system by electrode means;
  detecting a response signal generated by the said system using said electrode means;
  processing said applied signal and detected signal to provide data representative of a feature of the said system.

Preferably the method further comprises the step of transferring the said generated data to and storing the said generated data in a data storage means.

Preferably the method further comprises the step of applying a signal to the system wherein the signal comprises a plurality of different frequency waveforms.

Alternatively the method comprises the step of applying a single frequency signal to the system.

Conveniently the method comprises the step of applying a plurality of single frequency signals to the system and acquiring a plurality of detected signals corresponding to each of the respective applied signals.

According to a ninth aspect of the present invention there is provided a dentist's chair or light unit including an apparatus for detecting dental caries in a tooth comprising:
  means for generating an input electrical signal;
  means for applying the input electrical signal to the aforementioned tooth;
  means for detecting an output signal from the tooth to which the input signal was applied;
  means for receiving the output signal detected by the detecting means;
  means for analysing the input signal and output signal;
  wherein the means for analysing the input signal and output signal provides data representative of a feature of the tooth.

The data provided may be transmitted to and stored in data storage means.

According to a tenth aspect of the present invention there is provided a portable device for detecting a dental condition by generating an electrical signal to be applied to a system and acquiring a response signal generated by the system, the portable device comprising:
  signal generation means,
  signal receiving means, and
  signal processing means,
  wherein, in use, the device generates a signal to be applied to a system to be tested, and receives a response signal of the system which was tested whereby the applied and received signals undergo processing by the signal processing means to provide data indicative of a characteristic of the system.

Preferably the provided data is transferred to data storage means for storage.

Preferably tests carried out using the device generating a signal having a frequency in the range of 1 Hz-100 kHz provides accurate results for measurements made involving systems characterised by low frequency response such as high impedance media dental hard tissue and, for example, abrasion, attrition, caries, erosion or corrosion thereof or indeed any change in the tissue by any means, e.g. mechanical or chemical.

Herein the term "corrosion" includes at least chemical dissolution of dental tissues by bacterial degradation products, e.g. acids from low molecular weight sugars.

Further herein "erosion" includes at least loss of tooth substance by a chemical process that does not involve bacterial action. In other words, chemical dissolution of teeth by any other agent.

Herein further, "corrosion" includes at least oxidation or other changes of materials of fillings such as amalgam fillings, e.g. including: silver (Ag); copper (Cu); zinc (Zn); tin (Sn) and/or mercury (Hg).

The device may therefore find use in detection and/or measurement of primary or secondary caries or any other changes in natural or reconstructive dental materials.

It should be understood that the term "primary caries" includes an original carious lesion of a tooth and also should include all lesions not occurring adjacent to restorations, i.e. all non-secondary/non-recurrent caries.

Furthermore the term "secondary caries" includes caries which occur adjacent to a restoration.

Preferably tests performed using the device generating a signal(s) in a range above 100 kHz provides accurate results for measurements made involving systems characterised by high frequency response such as soft tissue or other low impedance media.

Medical Uses

According to a first aspect of the present invention there is provided use of a test equipment such as a portable test equipment or device in the detection of medical states or conditions, the device comprising:
signal generation means,
signal receiving means, and
signal processing means,
wherein, in use, the signal generation means generates an electrical signal to be applied to a medical system to be tested and the signal receiving means receives a response electrical signal of the system, and the generated and response signals undergo processing by the signal processing means so as to provide a measure of a characteristic of the system, wherein further the generated signal comprises a plurality of periodic signals each of different frequency and phase and which are applied to the system simultaneously.

The characteristic of the system may comprise an AC determined characteristic such as imittence, eg preferably impedance or alternatively admittance, permittivity or electric modulus.

Preferably the signal generation means comprises a signal assembly unit, which is software controllable, and operates at least in one mode according to an algorithm.

$$E_k = a_o \sum_{i=1}^{n} \sin(2\pi i f_0 t_k + \theta_i)$$

where $E_k$=voltage at any given time $t_k$,
$\theta_i$=phase randomised for each periodic signal so as to provide the plurality of periodic output signals.

Preferably each of the plurality of periodic signals comprises a sine wave.

Preferably the signal processing means performs a Fast Fourier Transform (FFT) analysis on the generated and response signals.

Preferably the phase of each of the plurality of periodic signals generated by the signal generation means is random.

Preferably one of the periodic signals has a frequency $f_o$, and each other periodic signal has a frequency which is a multiple of frequency $f_o$.

Preferably the generated signal is applied to the system for a period of time comprising $1/f_o$ or a multiple of $1/f_o$.

Preferably each point k of the generated signal is given by:

$$E_k = a_o \sum_{i=1}^{n} \sin(2\pi i f_0 t_k + \theta_i)$$

where $E_k$=voltage at any given time $t_k$,
$\theta_i$=phase randomised for each periodic signal.

Preferably there may be provided means to control the signal generation means.

Preferably the means to control the signal generation means may allow a user to select, switch or program the signal generation means to operate in a different mode and generate a different electrical signal(s), e.g. a single signal, e.g. a DC signal or a periodic signal such as a single sine wave.

According to a second aspect of the present invention there is provided use of a test apparatus such as a portable test apparatus in the detection of medical states or conditions, the apparatus comprising:
a test equipment according to the first aspect of the present invention;
electrode means which, in use, are applied to the system (eg patient body part) and/or patient so as to apply the generated signal to the system and receive the response signal from the system.

The electrode means are preferably applied to the system in a non-invasive and non-destructive manner.

According to a third aspect of the present invention there is provided a method of detecting medical states or conditions or state comprising the steps of:
providing a test apparatus according to the second aspect;
generating an electrical signal and applying said electrical signal to a system;
detecting a response electrical signal; processing the generated and response signals so as to provide a measure of a characteristic of the system.

According to a fourth aspect of the present invention there is provided use in the detection of medical conditions of a portable test device for generating an electrical signal to be applied to a system and acquiring a response signal generated by the system, the device comprising:
signal generation means,
signal receiving means, and
signal processing means,
wherein, in use, the device generates a signal to be applied to a system to be tested and receives a response signal of the system which was tested whereby the applied and received signals undergo processing by the signal processing means providing data representative of a characteristic of the system.

Preferably the data provided is then transferred to data storage means for storage.

Preferably the device may be hand held.

Preferably the device includes means for visually displaying data.

Preferably the device measures an impedance of the system.

Preferably the device is battery operated.

Conveniently the device may comprise means by which the device may be connected to a mains power supply to allow charging of the battery(ies) to take place.

Preferably the device may include means for associating the device with electrode means comprising at least a first electrode and a second electrode wherein the first electrode applies the generated signal(s) to the system(s) to be tested and the second electrode collects response signal from the system.

Most preferably the device includes means for ensuring connection to an external power supply and connection to electrode means cannot occur simultaneously.

Alternatively the device is configured or arranged such that connection to an external power supply and electrode means can occur simultaneously.

Preferably the signal applied to the system comprises at least one period of a periodic signal such as an AC signal.

Preferably the applied signal is formed of a plurality of periodic waves.

Conveniently each of the periodic waves is of a different frequency and random phase.

Preferably each of the waves is a sine wave.

Alternatively the applied signal is of a single frequency.

Preferably the applied signal is a sine wave.

Alternatively the applied signal is a square or other waveform (eg triangle, saw tooth or arbitrary).

Alternatively the signal applied to the system is a DC signal.

Preferably the means for analysing the applied signal and received signal performs Fast Fourier Transform (FFT) spectrum analysis upon the applied signal and received signal.

Preferably the signal receiving means includes data acquisition means.

Preferably the device may be used for detecting a medical condition in vivo.

Alternatively the device may be used for detecting a medical condition in vitro.

The device may be used in vivo or in vitro to measure or monitor a state of a material used in reconstruction of a body part such as a prosthetic, a metal or synthetic "pin" or the like, including corrosion or wear thereof.

Preferably the device is adapted or customised for specific end-use by embedded PC-based control software.

Conveniently the device may be programmed to perform a range of measurements with subsequent analysis, presentation, data storage and/or retrieval.

Preferably the device further comprises means for performing variable amplification on the received signal.

According to a fifth aspect of the present invention there is provided a method for detecting a medical condition by generating an electrical signal for application to a system and receiving the response signal generated by the system tested using a portable device, the method comprising the steps of:
generating a signal to be applied to the system;
detecting a response signal generated by the said system;
receiving said detected response signal;
processing said applied and received signals;
generating data indicative of a feature of the system from said processed signals.

Preferably the method further comprises the step of: storing the said generated data in data storage means.

Preferably the method includes the step of applying the generated signal to a system comprising at least in part biological materials or tissues, e.g. at least part of a human or animal body in vivo and acquiring a system response therefrom.

Conveniently the method may include the step of applying the generated signal to a system comprising at least a part of biological material or tissues, e.g. at least part of a human or animal body in vitro and acquiring a system response therefrom.

According to a sixth aspect of the present invention there is provided use of a portable apparatus for detecting a medical condition by applying electrical stimulus to a system and acquiring a system response, the apparatus comprising:
signal generation means,
signal receiving means,
signal processing means, and
electrode means which are, in use, applied to the system,
wherein a generated signal is applied to the system by said electrode means, a response signal of the system is detected by said electrode means and received by the signal receiving means, and the applied and received signals undergo processing by the signal processing means.

Preferably data generated by the signal processing means is transferred to data storage means for storage.

Preferably the signal processing means performs signal analysis on the generated signal and received signal.

Preferably the signal receiving means includes data acquisition means.

Conveniently the electrode means comprises one or more electrodes and may comprise an array of electrodes.

Preferably the apparatus is battery powered.

Conveniently the apparatus may be connected to an external power supply to allow charging of the battery to take place.

Preferably the apparatus is arranged such that the system may not be tested while the apparatus is connected to an external power supply.

According to a seventh aspect of the present invention there is provided a method for detecting a medical condition by performing electrochemical impedance measurements on a subject using a portable device, the method comprising the steps of:
generating a signal;
applying the generated signal to the subject by electrode means;
detecting a response signal generated by the said subject using said electrode means;
processing said applied and detected signals;
generating data indicative of a feature of the subject from said processed signals.

Preferably the method further comprises the step of transferring the said generated data to and storing the said generated data in a data storage means.

Conveniently the subject may by a human or animal.

Alternatively the subject may be another biological material or tissue.

Preferably the method comprises the step of applying a signal to the subject wherein the signal comprises a plurality of different frequency waveforms.

Alternatively the method comprises the step of applying a single frequency signal to the subject.

Conveniently the method comprises the step of applying a plurality of single frequency signals to the subject and acquiring a plurality of detected signals corresponding to each of the respective applied signals.

Preferably the method includes the step of applying an AC signal to the subject.

Preferably the method comprises the step of applying a 50 kHz simple sine waveform to the subject whilst performing measurements in vivo.

According to an eighth aspect of the present invention there is provided a portable device for detecting a medical condition by generating an electrical signal to be applied to a system and acquiring a response signal generated by the system, the portable device comprising:
signal generation means,
signal receiving means, and
signal processing means,
wherein the device generates a signal to be applied to a system to be tested, and receives a response signal of the system which was tested whereby the applied and received signals undergo processing by the signal processing means to provide data indicative of a characteristic of the system.

Preferably the data provided is transferred to data storage means for storage.

Preferably tests carried out using the device generating a signal(s) having a frequency in the range of 1 Hz-100 kHz provides accurate results for measurements made involving systems characterised by low frequency response such as bone or other hard tissue, or other high impedance media, including detecting the corrosion or erosion thereof.

Preferably tests performed using the device generating a signal(s) in the range above 100 kHz provides accurate results for measurements made involving systems characterised by a high frequency response such as soft tissue or other low impedance media.

Herein, the device may be used in vivo or in vitro to measure or monitor a state of material used in reconstruction of a body part, e.g. a prosthetic, or a metal or synthetic "pin" or the like, and for example the corrosion thereof.

According to a ninth aspect of the present invention there is provided use in the detection of clinical conditions of a portable device for generating an electrical signal to be applied to the system and acquiring a response signal generated by the system, the portable device comprising:
  signal generation means,
  signal receiving means,
  signal processing means, and
  analogue circuitry, wherein the analogue circuitry includes medical safety features which allows the device to perform tests in in vivo environments wherein the device generates the signal to be applied to a system under test and receive the response signal of the system which was tested whereby the applied and received signals undergo processing by the signal processing means, providing data indicative of a characteristic of the system.

Preferably the provided data is transferred to the data storage means.

Conveniently the safety features of the analogue circuitry conform to the appropriate International standard requirements for medical electrical equipment.

Preferably the device may be provided with only one input/output port wherein the device cannot be connected to an external power supply and a system to be tested simultaneously, particularly for in vivo work.

Other Uses

According to a first aspect of the present invention there is provided use of a test equipment such as a portable test equipment or device in the detection of conditions or states of non-dental/non-medical systems, the device comprising:
  signal generation means,
  signal receiving means, and
  signal processing means,
  wherein, in use, the signal generation means generates an electrical signal to be applied to a system to be tested and the signal receiving means receives a response electrical signal of the system, and the generated and response signals undergo processing by the signal processing means so as to provide a measure of a characteristic of the system, wherein further the generated signal comprises a plurality of periodic signals each of different frequency and phase and which are applied to the system simultaneously.

The characteristic of the system may comprise an AC determined characteristic such as imittence, eg preferably impedance or alternatively admittance, permittivity or electric modulus.

Preferably the signal generation means comprises a signal assembly unit, which is software controllable, and operates at least in one mode according to an algorithm:

$$E_k = a_o \sum_{i=1}^{n} \sin(2\pi i f_0 t_k + \theta_i)$$

where $E_k$=voltage at any given time $t_k$,
$\theta_i$=phase randomised for each periodic signal so as to provide the plurality of periodic output signals.

Preferably each of the plurality of periodic signals comprises a sine wave.

Preferably the signal processing means performs a Fast Fourier Transform (FFT) analysis on the generated and response signals.

Preferably the phase of each of the plurality of periodic signals generated by the signal generation means is random.

Preferably one of the periodic signals has a frequency $f_o$, and each other periodic signal has a frequency which is a multiple of frequency $f_o$.

Preferably the generated signal is applied to the system for a period of time comprising $1/f_o$ or a multiple of $1/f_0$.

Preferably each point k of the generated signal is given by:

$$E_k = a_o \sum_{i=1}^{n} \sin(2\pi i f_0 t_k + \theta_i)$$

where $E_k$=voltage at any given time $t_k$,
$\theta_i$=phase randomised for each periodic signal.

Preferably there may be provided means to control the signal generation means.

Preferably the means to control the signal generation means may allow a user to select, switch or program the signal generation means to operate in a different mode and generate a different electrical signal(s), e.g. a single signal, eg a DC signal or periodic signal such as a single sine wave.

According to a second aspect of the present invention there is provided use of a test apparatus such as a portable test apparatus in the detection of a non-dental/non-medical condition, the apparatus comprising:
  a test equipment according to the first aspect of the present invention;
  electrode means which, in use, are applied to a system so as to apply the generated signal to a system and receive the response signal from the system.

The electrode means are preferably applied to the system in a non-invasive and non-destructive manner.

According to a third aspect of the present invention there is provided a method of detecting a state or condition of a non-dental/non-medical system comprising the steps of:
  providing a portable test apparatus according to the second aspect of the present invention:
  generating an electrical signal and applying said electrical signal to the system;
  detecting a response electrical signal;
  processing the generated and response signals so as to provide a measure of a characteristic of the system.

According to a fourth aspect of the present invention there is provided use of a portable test device for measuring at least one property of a system, other than a dental or medical system, by generating an electrical signal to be applied to a system and acquiring a response signal generated by the system, the device comprising:
  signal generation means,
  signal receiving means, and
  signal processing means,
  wherein, in use, the device generates a signal to be applied to a system to be tested and receives a response signal of the system which was tested whereby the applied and received signals undergo processing by the signal processing means providing data indicative of a characteristic of the system.

Preferably the provided data is transferred to data storage means for storage.

Preferably the device may be hand held.

Preferably the device includes means for visually displaying data.

Preferably the device measures an impedance of the system.

Preferably the device is battery operated.

Conveniently the device may comprise means by which the device may be connected to a mains power supply to allow charging of the battery(ies) to take place.

Preferably the portable device may include means for associating the device with electrode means comprising at least a first electrode and a second electrode wherein the first electrode applies the generated signal to the system to be tested and the second electrode collates response signal(s) from the system response.

Preferably the device is configured or arranged such that connection to an external power supply and electrode means cannot occur simultaneously.

Alternatively the device is configured or arranged such that connection to an external power supply and electrode means can occur simultaneously.

Conveniently the device is provided with safety features conforming to an appropriate Standard requirements for electrical equipment.

Preferably the device may be provided with only one input/output port wherein the device cannot be connected to an external power supply and a system to be tested simultaneously.

Alternatively the device may be provided with two or more input/output ports wherein the power to the device and the signals transferring to and from the device are assigned to individual input/output ports.

Preferably the signal applied to the system comprises at least one period of a periodic signal such as an AC signal.

Preferably the applied signal is formed of a plurality of periodic waves.

Conveniently each of the periodic waves is of a different frequency and random phase.

Preferably each of the waves is a sine wave.

Alternatively the applied signal is of a single frequency.

Alternatively the applied signal is a square waveform or other waveform (e.g. triangle, saw tooth or arbitrary).

Preferably the applied signal is a sine wave.

Alternatively the signal applied to the system may be a DC signal.

Preferably the means for analysing the applied signal and received signal performs Fast Fourier Transform (FFT) spectrum analysis upon the applied signal and received signal.

Preferably the device is adapted or customised for specific end-use by embedded PC-based control software.

Conveniently the device may be programmed to perform a range of measurements with subsequent analysis, presentation, data storage and/or retrieval.

Preferably the device further comprises means for performing variable amplification on the received signal.

Preferably the signal receiving means includes data acquisition means.

According to a fifth aspect of the present invention there is provided a portable apparatus for use measuring at least one property of a system, other than a dental or medical system, by applying electrical stimulus to a system and acquiring a system response, the apparatus comprising:

signal generation means,
signal receiving means,
signal processing means, and
electrode means which, in use, are applied to the system, wherein a generated signal is applied to the system by said electrode means, a response signal of the system is detected by said electrode means and received by the signal receiving means, and the applied and received signals undergo processing by the signal processing means.

Preferably data generated by the signal processing means is transferred to data storage means for storage.

Preferably the signal processing means performs signal analysis on the generated signal and received signal.

Conveniently the electrode means comprises one or more electrodes and may comprise an array of electrodes.

According to a sixth aspect of the present invention there is provided a method of electrochemical impedance measurement on a system, other than a dental or medical system, using a portable device, the method comprising the steps of:

generating a signal;
applying the generated signal to the system by electrode means;
detecting a response signal generated by the said system using electrode means;
processing said applied signal and detected signal and generating data representative of a feature of property of the system from said signal processing.

Preferably the method further comprises the step of transferring the said generated data to and storing the said generated data in a storage means.

Preferably tests carried out using the device generating a signal having a frequency in the range of DC-100 kHz provides accurate results for measurements involving systems characterized by low frequency response such as polymers, dielectrics and electrode processes or other high impedance media.

Preferably tests performed using the device generating a signal in a range above 100 kHz provides accurate results for measurements made involving systems characterised by high frequency response such as highly conducting electrolytes or other low impedance media.

BRIEF DESCRIPTION OF DRAWINGS

These and other aspects of the present invention will become apparent from the following description when taken in combination with the accompanying drawings, which are:

FIG. 7a a schematic representation of analogue input and output channels of the portable device of FIG. 3a;

FIG. 8a a schematic representation of an interface panel of the portable device of FIG. 3a;

FIG. 18b a schematic representation of the dental diagnostic instrument of FIG. 18(a), in use;

FIGS. 20a,b,c,d selected screen displays which may be shown on a screen of the portable device of FIG. 2;

DETAILED DESCRIPTION OF DRAWINGS

Figure 1:
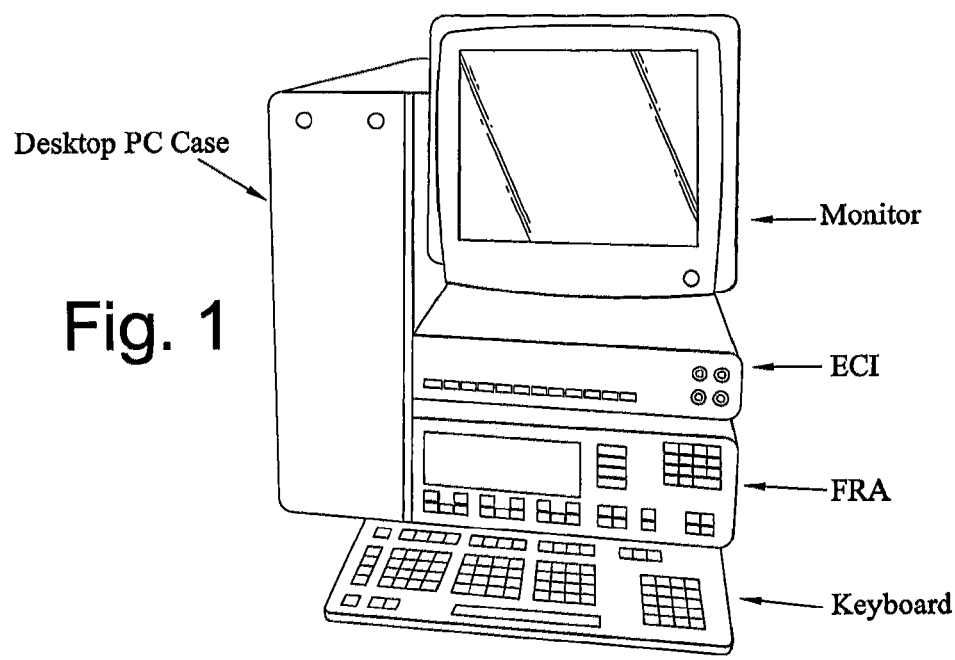
FIG. 1 a previous laboratory arrangement for performing measurement of impedance spectra.
Figure 2:
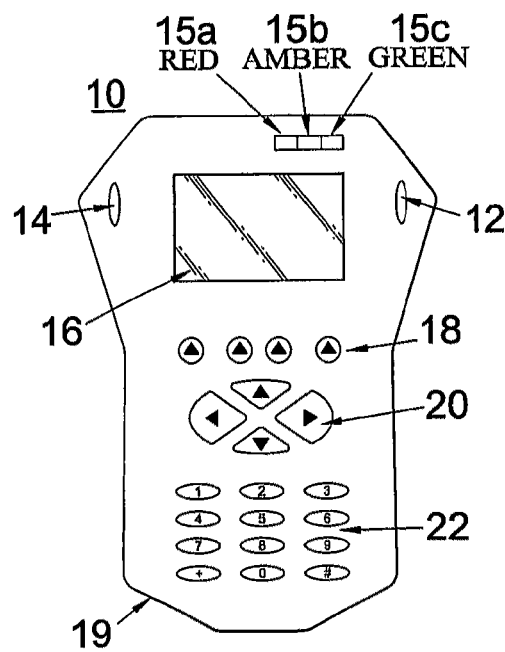
FIG. 2 a front casing of a portable device according to a first embodiment of the present invention.

With reference to FIG. 2 there is shown a front face of test equipment comprising a portable, e.g. hand held, diagnostic device 10 according to a first embodiment of the present invention. The device 10 comprises a housing 19, upon the surface of which is disposed an 'OK' button 12, a cancel button 14, cursor keys 20, an alpha-numeric keypad 22, programmable soft keys 18, and a graphical LCD screen 16 and LEDs 15a, b and c which are red, amber and green, respectively. The LED's 15a, b and c provide a visual indication of the state of operation of the device 10. At a top end of the housing 19 is provided a panel on which is provided appropriate signal transfer interfaces, depending on the proposed use of the device 10. The device 10 is a data acquisition device which is battery powered, in this case by a rechargeable Li-ion unit.

Figure 3A:
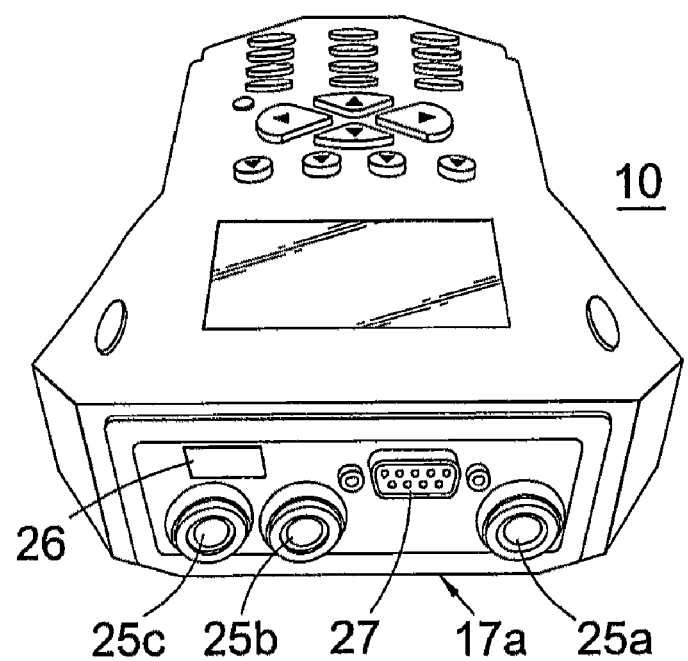
FIG. 3a an end view of the portable device of FIG. 2 according to a first implementation.

In FIG. 3a there is shown an end view of a first implementation of the device 10 in which can be seen interface panel 17a on which is provided input/output (I/O) ports 25a, 25b, and 25c, infra red data association (iRda) port 26 and RS-232 port 27. I/O ports 25b and 25c provide connection to means, such as electrodes, for performing measurements. I/O port 25a provides connection to a power supply for either directly powering the device 10 or for recharging the device battery. RS-232 port 27 provides connection means for hardwire transfer between the memory of the device 10 and a remote PC (not shown). The information transferred by a cable attached to this port 27 can be used in conjunction with information transferred using the iRda port 26.

Figure 3B:
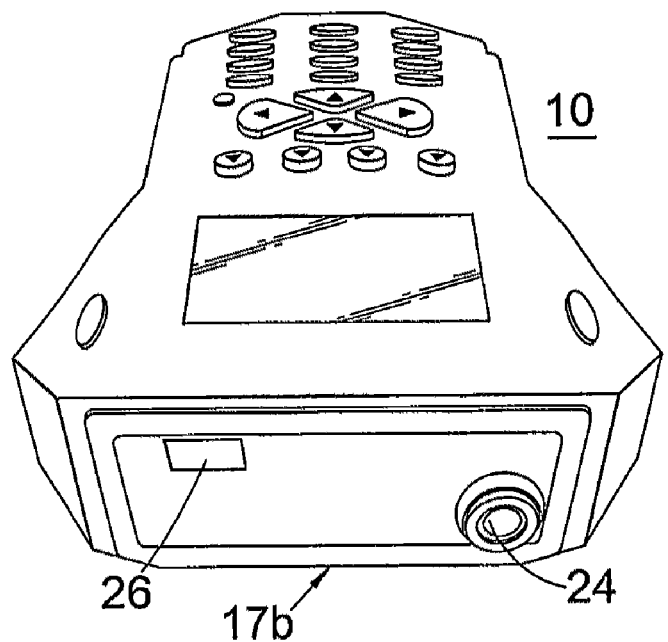
FIG. 3b an end view of the portable device of FIG. 2 according to a second implementation.

In FIG. 3b is shown an end view of a second implementation of the device 10 having interface panel 17b on which is disposed a 12-way I/O port 24 and an iRda port 26 which can allow wireless data transfer to and from non-volatile memory of the device 10 and an associated PC system (not shown), for example, a desktop system.

In the arrangement shown in FIG. 3b, the device 10 is arranged for use, in particular but not exclusively, performing in vivo measurements such as medical or dental measurements as only one I/O port 24 has been provided on interface panel 17b. I/O port 24 can provide connection to electrodes thus allowing measurements to be performed, or can provide connection to a power supply thus allowing the device battery to be recharged. The provision of only one I/O port 24 means these functions can only be performed exclusively, ie not simultaneously, and therefore the device 10 is suited to in vivo use as at no time would a patient be in direct contact with a mains power source or other external power supply including a mains powered device.

Figure 4:
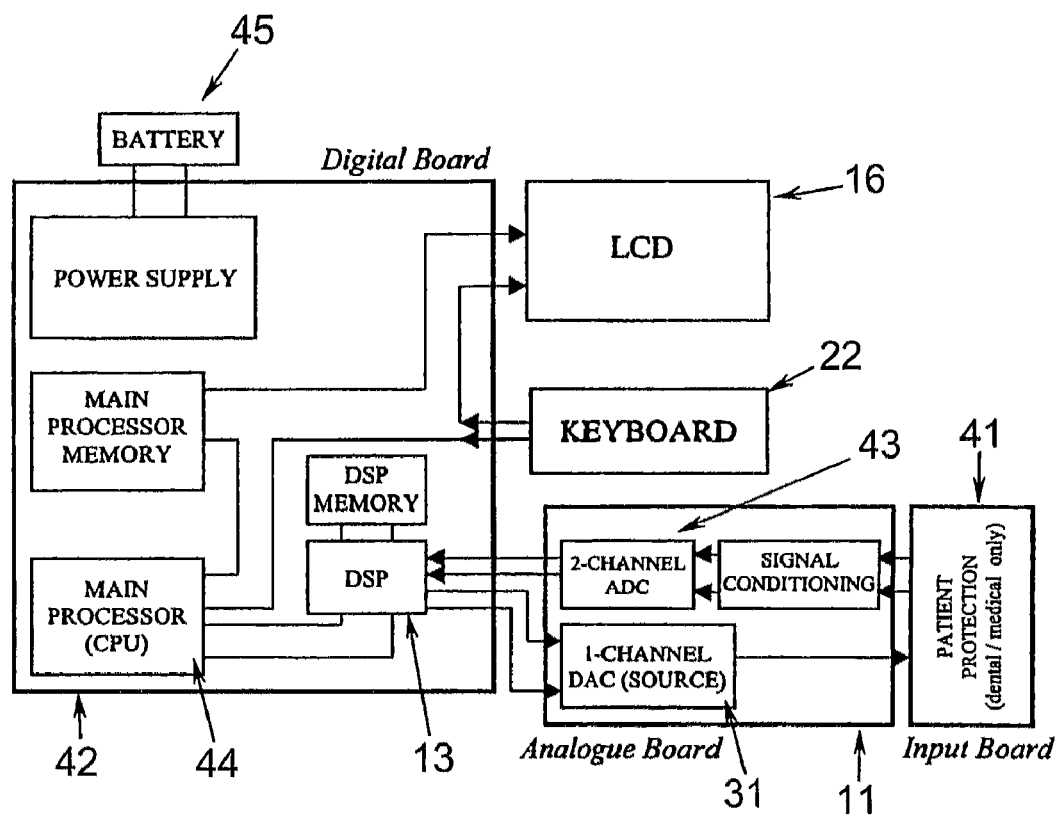
FIG. 4 a block diagram of internal components of the portable device of FIG. 2.

In FIG. 4 there is shown a simplified block diagram of hardware of the device 10 which is integrated within the device housing 19. The hardware comprises analogue circuitry 11, rechargeable battery 45, digital board 42 including digital signal processor (DSP) 13 and data storage means. The data storage means are, in this case, Flash memory where data acquired by the device 10 is stored after processing.

Figure 5:
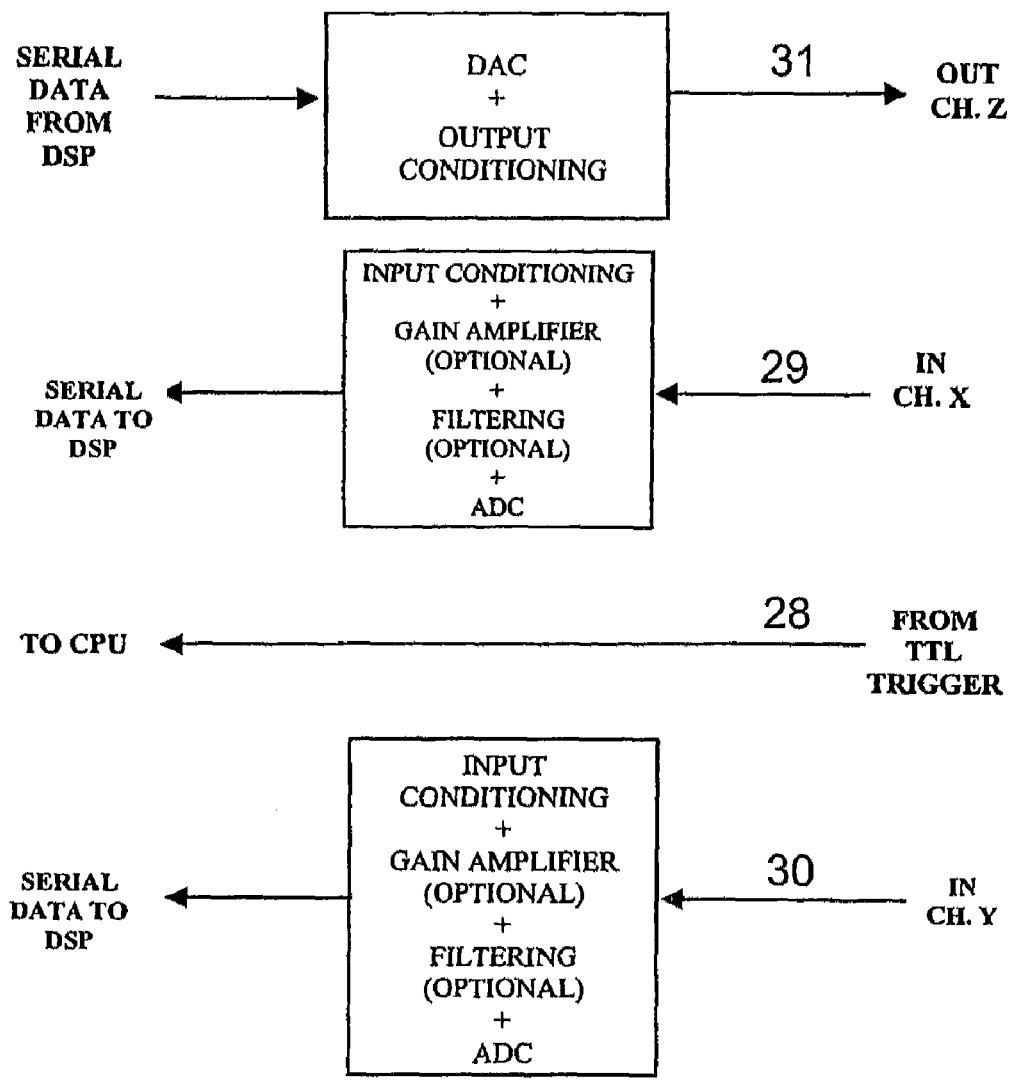
FIG. 5 a simplified block diagram of input and output channels of the portable device of FIG. 2.

With reference to FIG. 5 there is shown a simplified block diagram representative of interconnection of the analogue circuitry 11 of the device 10 and illustrates signal source, output channel 31, analogue input channels 29 and 30 and the respective operations which are performed on each of these channels. Also illustrated is a digital trigger 28 which, for example, is a remote switch, fire button or some other appropriately connected digital stimulus.

Figure 6:
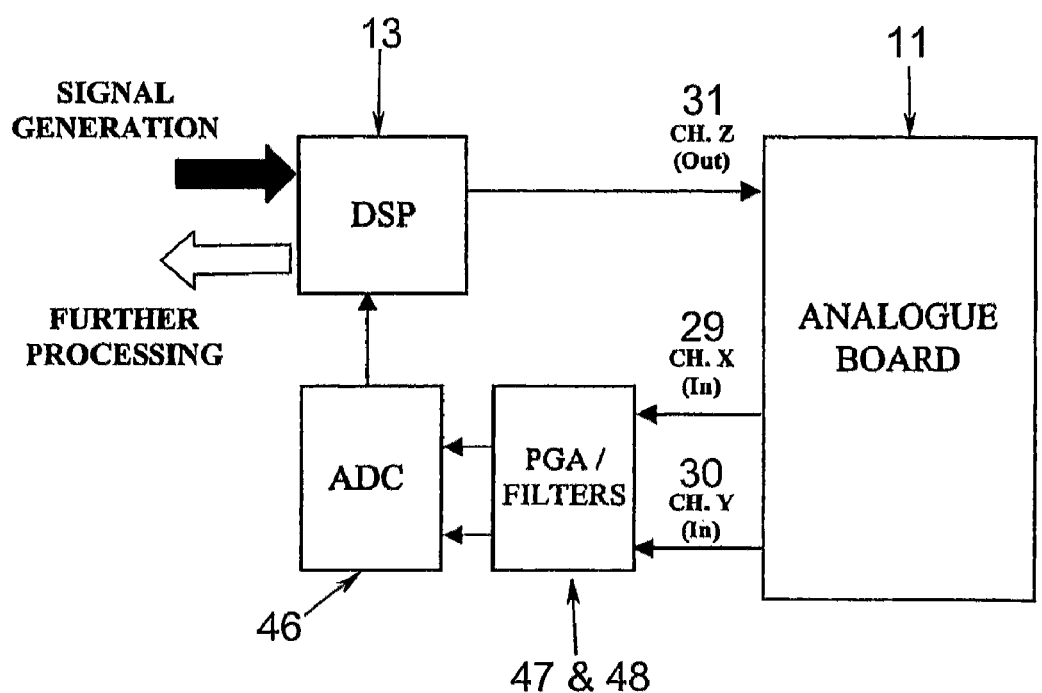
FIG. 6 a simplified block diagram representative of interconnection of a digital signal processor and analogue circuitry of the portable device of FIG. 2.

In FIG. 6 there is shown a simplified block diagram which illustrates interconnection between the digital signal processor (DSP) 13 and the analogue circuitry 11 of the device 10. A software application embedded within the device 10 creates an output signal which is generated by the DSP 13 and is carried as serial data on output channel 31 to analogue circuitry 11 from where it is applied to a system to be tested and also redirected in order to return to the DSP 13 for use in data analysis. The redirected output signal and detected response signal from the test system are carried from analogue circuitry 11 by channels 29 and 30 respectively, through a further programmable gain amplifier 47 and filtering stage 48 respectively, then to an analogue to digital converter (ADC) 46 back to the DSP 13 where they undergo signal analysis, such as transfer function and FFT, for EIS measurements performed over a wide range of impedance and/or frequency.

Figure 7A:
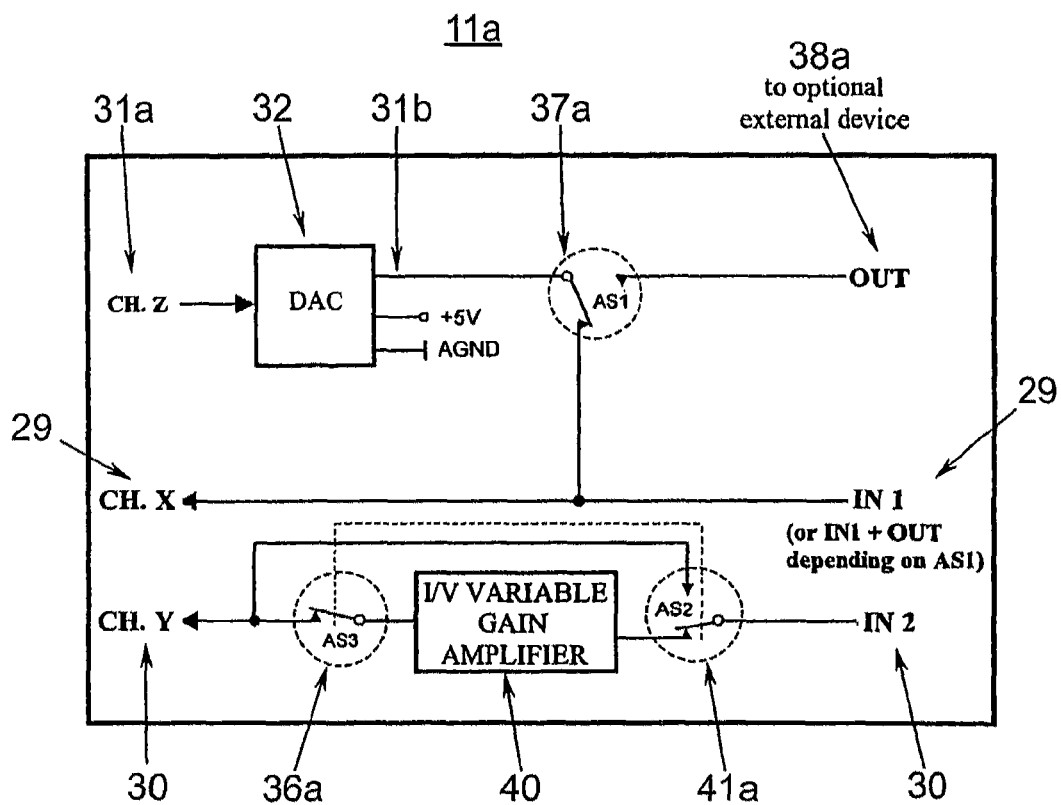

In FIG. 7a there is shown analogue circuitry 11a corresponding to the device 10 being provided with interface panel 17a. In this arrangement, the analogue circuitry 11a of the device 10 has a signal source output channel 31a which provides the generated signal to digital-to-analogue (DAC) converter 32, the analogue signal output from which is either applied to the system to be tested, (e.g. a dental system such as a whole tooth in vivo or in vitro, a medical system or another system, e.g. a battery), via output 38a or is directed by AS1 switch 37a to input/output channel 29. The response signal generated by the tested system is carried on input channel 30 where it can be directed through, or allowed to by-pass a programmable variable gain amplifier 40 by means of AS2 switch 41a. Switch AS3 36a is included in input channel 30 to prevent back drive of high voltage from the amplifier 40 through switch 41a to the system being tested and the operation of this switch is coupled to switch AS2 41a for this reason. This circuitry 11a further shows that by wiring CH.Z 31a to CH.X 29, external noise is incorporated back from IN1 29 (or COUNTER 34 in circuitry 11b). This "common mode noise" is thus removed on execution of transfer function (CH.X/CH.Y) required for an impedance measurement. Such an analogue circuit arrangement is suitable for use performing tests in systems such as batteries, coatings, stress detection in civil engineering fields etc wherein the device can perform measurements whilst battery powered. However, tests may also be performed whilst the device is connected to a mains power supply or mains powered device.

Figure 7B:
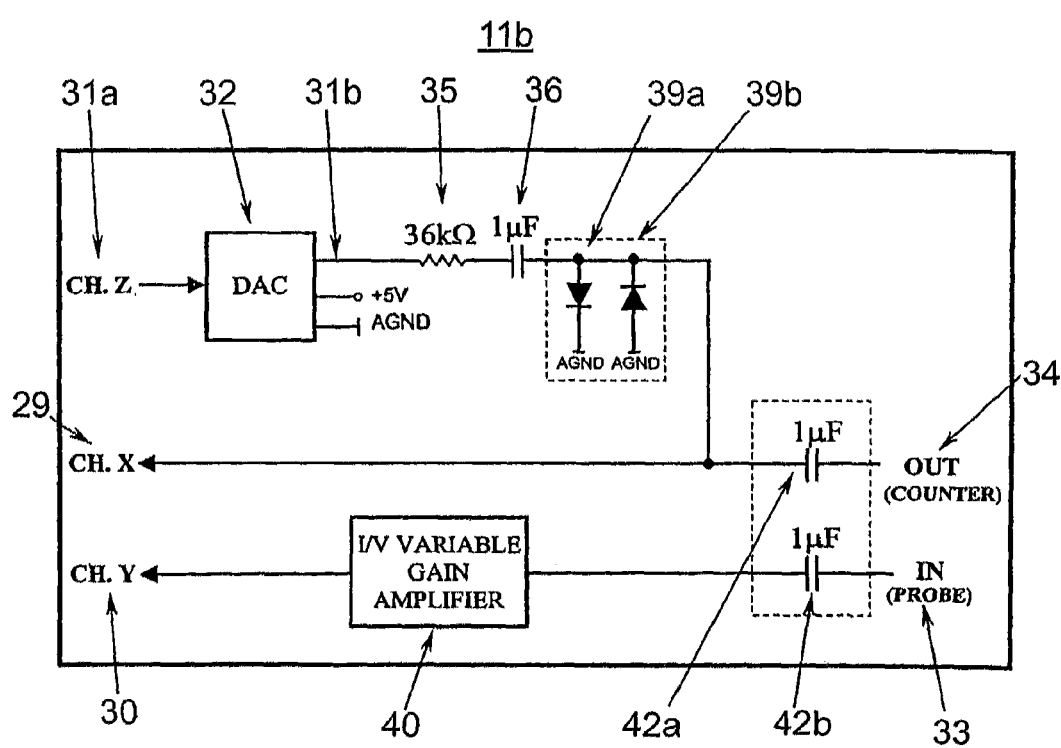
FIG. 7b a schematic representation of analogue input and output channels of the portable device of FIG. 3b.

In FIG. 7b there is shown analogue circuitry 11b corresponding to the device 10 being provided with interface panel 17b. In this arrangement the analogue circuitry 11b is provided with a signal source output channel 31, which provides the generated analogue output signal to be applied to the system being tested. The circuitry 11b further comprises analogue input channels 29 and 30 into which is input the generated signal and detected response signal respectively. The output channel 31 implements the output provided by a digital signal source and includes digital to analogue converter (DAC) 32.

The generated analogue output signal, which in this case is a multi-sine wave, is passed from output channel 31 to, in this case counter electrode 34, which is connected to the system being tested, for example, a patient under study. A response signal from the probe or working electrode 33, which is connected to another site on the test system, for example a tooth, is directed through a programmable variable gain amplifier 40 which may amplify the signal by a factor from the range of for example x1 to $x10^9$, and typically $x10^5$ before reading the amplified signal to input channel 30. The output signal carried on output channel 31 is also directed back into the input channel 29 thus allowing use of the source wave in data analysis. As can be seen, medical safety features conforming to British, European and IEC standard requirements for medical electrical equipment that allow safe use of the device 10 in vivo are incorporated into the analogue circuitry 11b. On the end of the output channel 31 which connects to counter electrode 34, there is provided a 36 KΩ resistor 35, which limits the current transmitted to the counter electrode 34 to below 20 µA. Furthermore, a 1 µF DC blocking capacitor 36 and voltage clipping diodes 39a and 39b are placed in series with resistor 35 which starts to clip the maximum voltage amplitude passing to counter electrode 34 at 500 mV. Similarly, 1 µF DC blocking capacitors 42a and 42b are provided on signal input channels 29 and 30 respectively at the test system side of circuit 11b. In order for the device to meet the voltage limits under single fault conditions, high voltage sources, such as the battery charger input and RS-232 port are isolated from the test system whilst system measurements are being made. This is achieved by the provision of only one 12-way I/O port 24 being constructed as shown in FIG. 3b to overcome medical safety issues regarding clinical measurements by ensuring that any person on which measurements are being made is safely isolated from a mains AC power supply. Additionally, any power source dedicated to generating a backlight in the display of the device is disabled within the hardware.

Figure 8A:
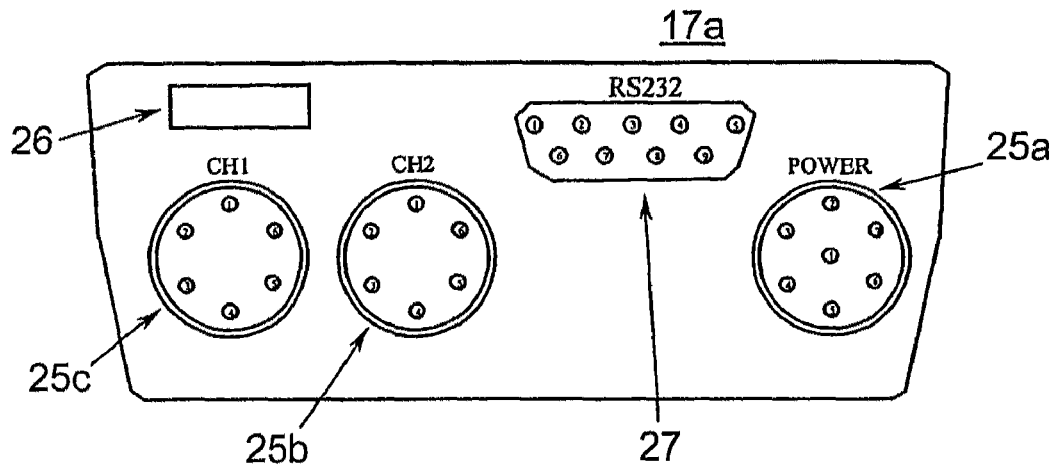

A schematic diagram of the interface panel 17a having I/O ports 25a, 25b and 25c, RS232 port 27 and IRDA port 26 which is used when the device 10 is provided with the analogue circuitry 11a is shown in FIG. 8a. Each of the pins of the I/O ports and RS232 port are enumerated with pin number 1-7, 1-6, 1-6 and 1-9 respectively. The detailed pin configurations are examples only and all the connections can be customised for specific end uses.

Figure 8B:
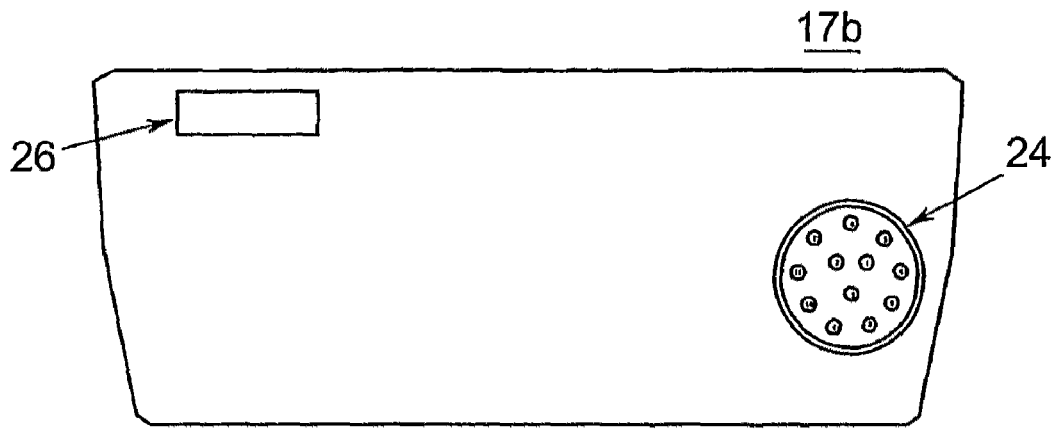
FIG. 8b a schematic representation of an interface panel of the portable device of FIG. 3b.

In FIG. 8b there is shown a schematic diagram of the interface panel 17b having I/O port 24 which is used when the device 10 includes the safety features of analogue circuitry 11b. Each of the pins has been enumerated with pin numbers 1 to 12. The function assigned to each of these pins is as follows:

Pin 1 is assigned the RS232 DTR function, which connects Pin 1 to Pin 6. The DTR function is Data Terminal Ready and is driven by the Data Terminal Equipment (DTE) i.e. the PC when it is ready for action.

Pin 2 is assigned to analogue input channel 30.

Pin 3 is assigned to analogue output channel 31.

Pin 4 is assigned to external (EXT) TTL trigger 28 with the trigger operating between 0 to 5 V.

Pin 5 is assigned to an AGND function, which is Analogue ground.

Pin 6 is assigned to a RS232 DCD\DSR function. The DCD function is Data Carrier Detect and is driven by the Data Circuit terminating Equipment (DCE) i.e. a modem or other peripheral. For a modem, this indicates that the line signal is being received, for other peripherals it means that they are ready to transmit. A DSR signal indicates the device 10 is powered up and ready to transmit.

Pin 7 is assigned to a RS232 TxD OUT function, where TxD is "Transmit Data" and this carries data to and from the RxD pin.

Pin 8 is assigned to a RS232 RxD IN function, where RxD is "Receive Data" and this carries data to and from the TxD pin.

Pin 9 is assigned to a RS232 CTS IN function where CTS is "clear to send" and a signal on this pin indicates the device is ready to accept data.

Pin 10 is assigned to a RS232 RTS OUT function where RTS is "ready to send" and indicates the device is wanting to send data; the modem, or other peripheral, responds by switching its CTS line on when ready to accept.

Pin 11 is assigned to a EXT DC IN function which is a 12V DC input.

Pin 12 is assigned to a DGND function which is a Digital ground.

By combining all I/O connections into a single port and constructing an individual cable for each I/O operation, the device 10 is physically prohibited to be simultaneously connected to a mains AC powered device or supply while also connected to a patient for in vivo measurement.

As the device 10 is capable of performing several operations, for example, taking measurements, performing analysis, database storage, transfer of data by various means such as RS232, and charging/monitoring of battery, depending on the software application embedded into the ROM of the device 10 there are at least three cables required to perform all operations.

Figure 9A:
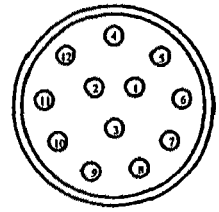
FIGS. 9a,b,c schematic views of cable configurations required for operating the portable device of FIG. 2 in different function modes.
Figure 9A:
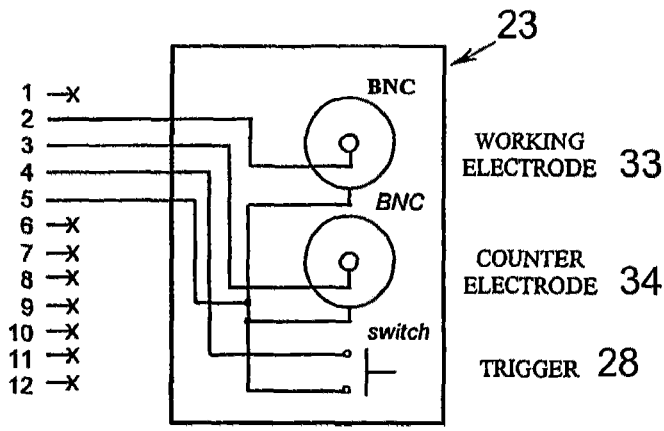
Figure 9B:
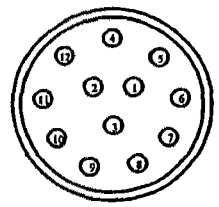
Figure 9B:
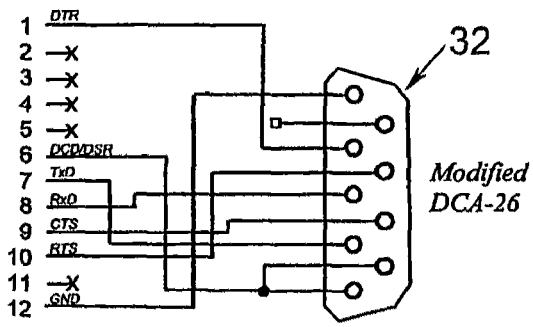
Figure 9C:
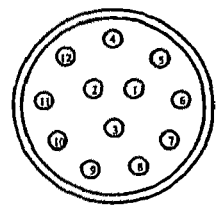
Figure 9C:
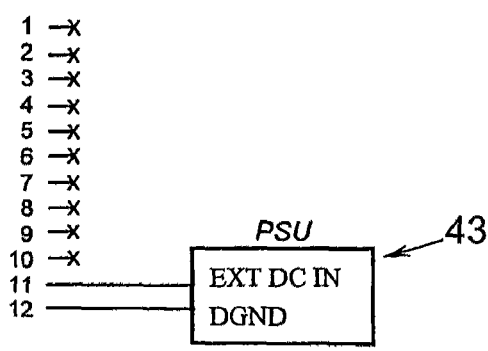

In FIGS. 9a, 9b and 9c there are shown three embodiments of cable construction each one capable of performing a different operational function when connected to device 10 having circuitry 11b via I/O port 24. In this case, the cable illustrated is a 12-way port commercial socket from Fischer.

With reference to FIG. 9a there is shown the cable construction of the signal cable which is used when connecting device 10 to a system to be tested, and in this case is constructed in a manner that provides BNC connection for channels 29 and 30 respectively. Trigger 28, is in this case a switch provided remotely, as a "fire" button, upon operation of which an output signal is generated by the DSP 13, and is connected to pin 4 and pin 5 as well as to the BNC connections for channels 29 and 30.

The signal cable construction shown in FIG. 9b allows hardware transfer between the flash memory of device 10 and a remote PC. In this case the cable shown for this operation is wired for connection to a Modified DCA-26, which is a standard 9 pin serial plug modified to overcome standard wiring configurations, with pins 1, 6, 7, 8, 9, 10 and 12 of I/O port 24 being assigned as detailed with reference to FIG. 8b. The information transferred by this cable can be used in conjunction with information transferred by, for example, using the IRDA port 26.

The cable shown in FIG. 9c allows the charging of the battery when connecting the I/O port 24 to an external power supply unit 43. This operation involves pins 11 and 12 providing DC input and digital ground functions respectively.

In order to allow device 10 to be used for a specific application in vivo environment, custom software is embedded into the memory system of the device 10 thus allowing the user to be provided with a specialist measurement without any need to modify the hardware characteristics of the device 10. Alternative software is embedded within the memory system of the device 10 if it is to be used in alternative specialist uses.

Figure 10A:
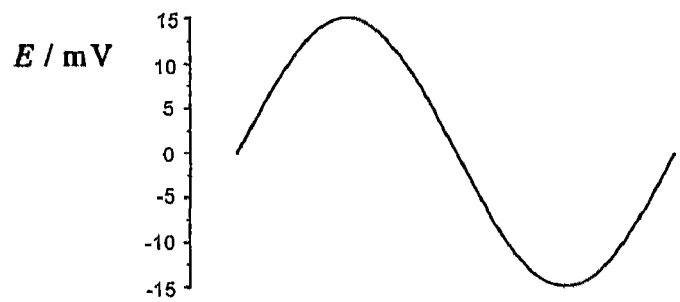
FIGS. 10a,b,c,d schematic representations of component waveforms and the resultant constructed "pseudo-random noise" waveform suitable for use in the present invention.

Typically the device operates in an Electrochemical Impedance Spectroscopy (EIS) mode with, for example, the EIS operations performed using a multi-sine method. The construction of a "pseudo-random noise" output waveform which is used in the preferred EIS measurement mode to be carried out by the device 10 is shown in FIGS. 10a to 10d. The waveform is constructed using sinusoids based on a fundamental sine wave of 15 mV amplitude and having fundamental frequency $f_o$ of say 100 Hz which is shown in FIG. 10a.

The pseudo-random noise source waveform, is constructed by a summation of n sinusoids based on the user defined fundamental lower frequency $f_0$ and an upper frequency $f_n$ (=n·$f_0$) and amplitude $a_0$, each with random phase.

In practice, each point k of the voltage waveform is generated according to the function:

$$E_k = a_o \sum_{i=1}^{n} \sin(2\pi i f_0 t_k + \theta_i)$$

where $E_k$=voltage at any given time $t_k$, and $\theta_i$ is the phase randomised for each sinusoid. The peak-to-peak amplitude of the voltage perturbation signal could be adjusted by multiplying $E_k$ with appropriate coefficients applied by multiplying the resulting waveform by an appropriate value in the software.

Figure 10B:
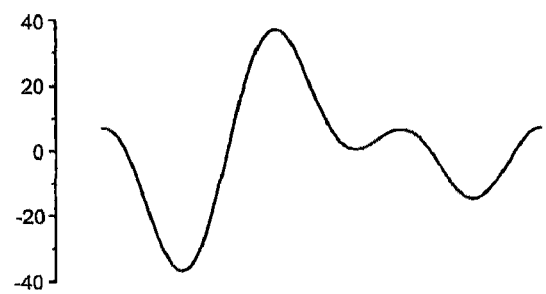
Figure 10C:

The waveforms generated by the summation of three sines representing 100 Hz to 300 Hz is shown in FIG. 10b, and the waveforms generated by the summation of ten sines representing 100 Hz to 1 KHz are shown in FIG. 10c. As can be seen these already resemble random patterns.

Figure 10D:
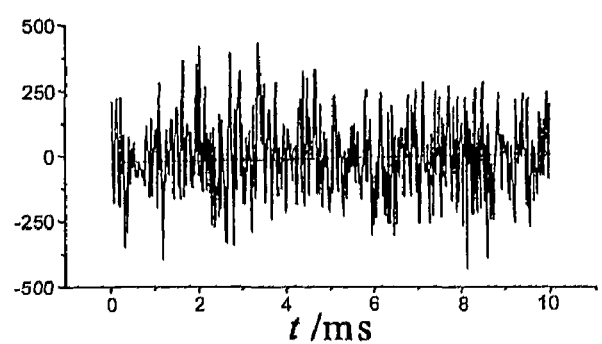

In FIG. 10d the waveform generated for a frequency range of 100 Hz to 20 KHz is the result of 200 overlapping sines and this provides a waveform resembling white noise. The time period for each of the waveforms shown in FIGS. 10a to 10d is ten milliseconds. Typically, in the performance of a measurement made using the device 10 the entire signal measurement is completed in a full cycle period of the lowest frequency, that is the applied duration of the source waveform on output channel 31 is (1/$f_O$) seconds, which in the case of FIG. 10d, is 10 ms. This means the entire measurement experiment time, including analysis, can be completed in approximately 3 seconds.

The use of the multi sine signal, which has a root mean square voltage of 35% of the selected peak amplitude, means that measurements taken by the system are exposed to less severe perturbations than measurements taken using a series of discrete sine waves as these typically have a root mean square voltage of 70% of the selected peak amplitude. This advantage is of particular importance at lower frequencies where measurement periods are longer and the possibility of corrupting the system during measurement is high.

In order for a measurement to be taken using the device 10, the I/O channels 29,30 and 31 and the digital signal processor 13 must be initialised. The software application embedded within the device 10, regardless of the functionality it imposes upon the device 10, runs an initialisation routine, typically when an instance of the program is first executed. Upon being switched on, device 10 will power up with the software application instance already running and therefore already present.

Figure 11:
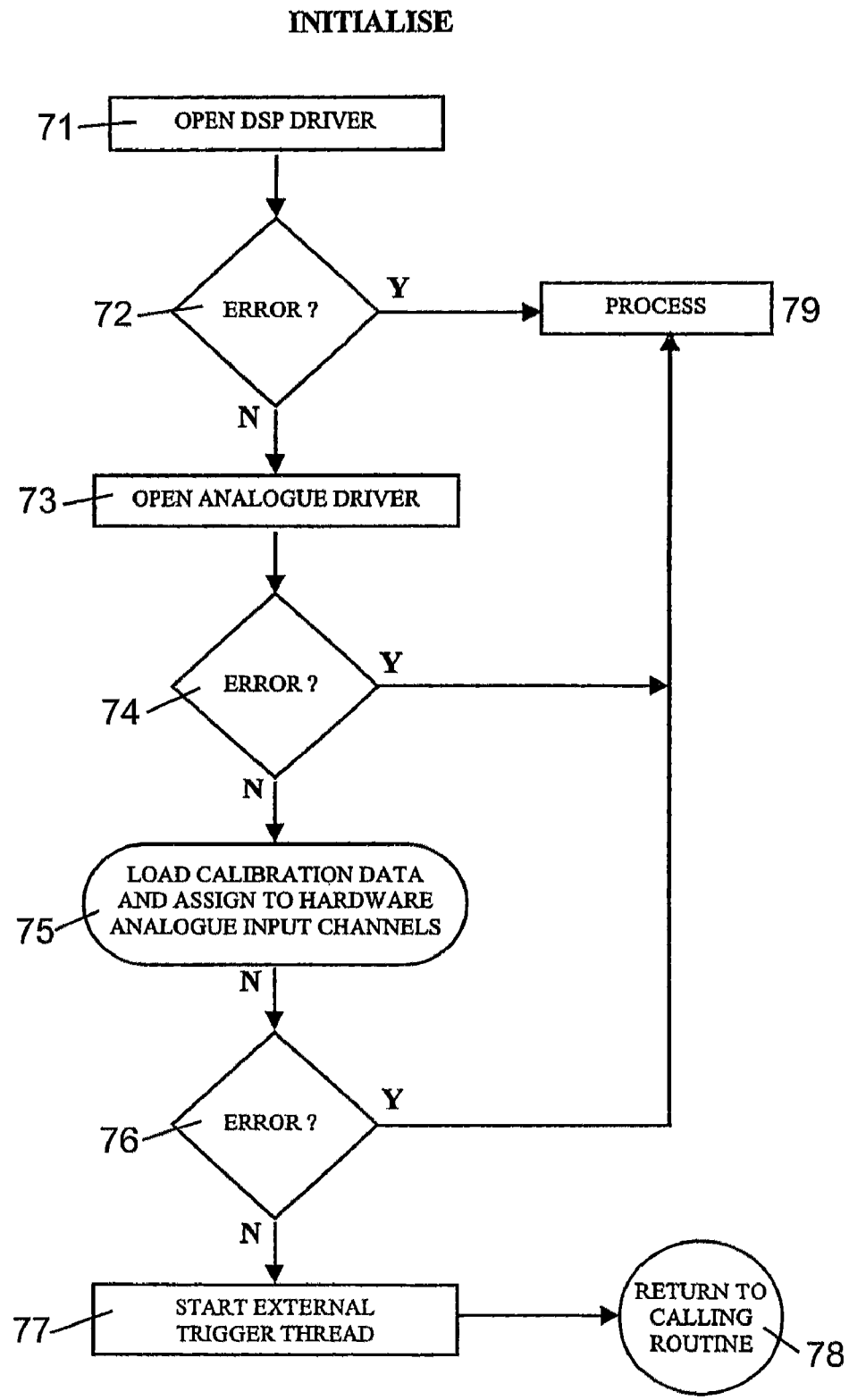
FIG. 11 a flow diagram of an initialisation routine for hardware of the portable device of the present invention.

A flow diagram of the initialisation routine common to each software application is shown in FIG. 11. Upon initialisation, the DSP driver file, which is stored in the flash memory of the device 10, is opened and the relevant software code, which is a data file stored in Flash that has controlling software functions, is read into a buffer, stored within a software array, where it is manipulated before being sent to DSP as serial data in the correct format for receiving. This process is represented by step 71 of the flow diagram. Similarly, as can be seen in step 73, an analogue driver file is also loaded from Flash memory into the application of embedded software which is currently running. Each of the analogue input channels 29 and 30 has a corresponding calibration file which is a data file storing calibration data which is loaded from the Flash memory. Information from each data file is read by the software application and sets up the appropriate tolerances of coarse offset, fine offset and factor values. The software handles, which are variables in software representing the input and output channels, are then assigned to the physical channels 29, 30 and 31 on the analogue circuit board 11. The initialisation process is checked for errors at steps 72, 74 and 76 and any errors are processed by the software application and retries are made at each step if not successful on the previous attempt. A suspended worker thread is started at step 77 for the external digital trigger 28 and operates in the background upon completion of the calibration data concluding successfully. Once resumed from the suspended mode in which it was started, at a point in the application where triggering is required, for example, if a measurement is to be taken, the external trigger thread will execute. This happens when an event occurs that is triggered by the external digital trigger 28, which is for example a fire button or some other appropriately connected digital stimulus. The return to calling routine step 78 occurs when the software function ends.

Figure 12:
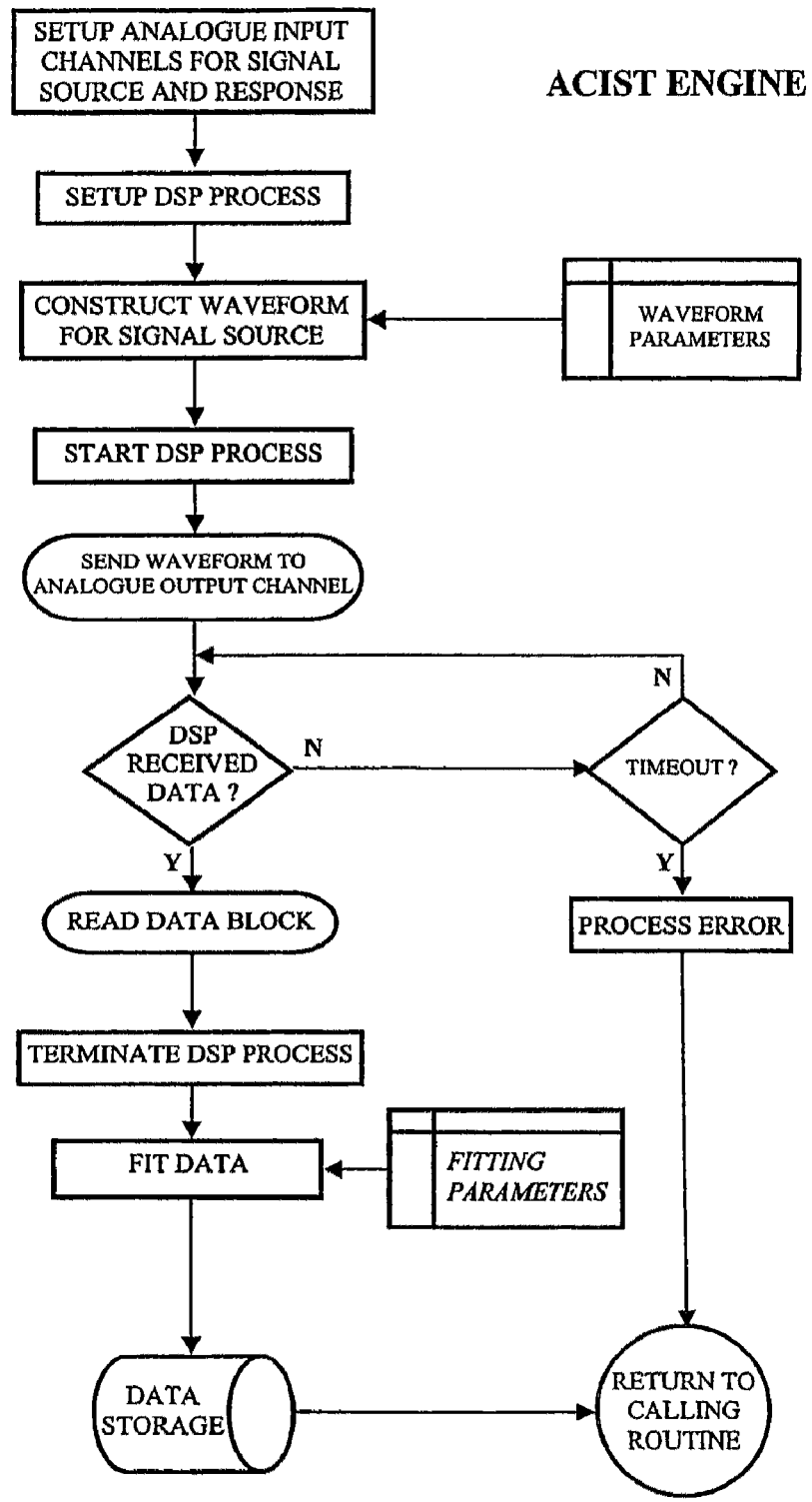
FIG. 12 a flow diagram representative of a measurement routine called the ACIST Engine™ for the portable device of the present invention.

With reference to FIG. 12 there is shown a flow diagram of the routine which is performed by the device 10 when taking an EIS measurement, also known as an ACIST™ measurement. The software for performing such a measurement is termed "ACIST Engine™". The flow diagram represents the core operation which allows the device 10 to acquire EIS data. The analogue source channel 31 is assigned a software handle then set up with a high pass filter enabled. The sample rate is sufficiently high to accurately represent the waveform of FIG. 10d without liasing at its highest frequency component. The response channel 30 is assigned a unique software handle and the programmable gain stages of the variable gain amplifier 40 are set before all the setup information data is flushed to the DSP 13. The DSP process is first set up by software in a manner similar to the set up operation of the analogue hardware channels, by specifying the average number of measurements to be taken during an experiment, that is any single measurement of a sample or system. Following this, the measurement type is specified as a transfer function by the embedded software application, and the number of points is given. Windowing is then selected if required, however, in the case of the present EIS experiment none are chosen.

The DSP process is started upon the generation of a waveform, such as that shown in FIG. 10d, which is sent to the analogue output channel 31 as a serial data block. The routine, sets up a software timer and waits for data to be received from the analogue input channel 30 at the DSP 13, that is it waits for the response data from the tests carried out. If no response data is received within the specified timeout period determined by the software timer, the user receives an indication of the problem, typically via the display screen 16. However, if response data is successfully received and read by the DSP 13, the real and imaginary parts of impedance, as well as coherence information, are read into a buffer array in the software from the data block, in this case as a fixed length of serial response data from the DSP 13. The DSP process is then terminated and the measurement data is passed to an appropriate fitting routine defined in the software application and which can call appropriate models from Flash memory for use to provide a target function, that is a mathematical model representing the physical properties of the system under test, from those of a chosen equivalent circuit model. The received response data and fitted parameters are then stored by a persistent data storage routine which saves data to the Flash memory for later retrieval to be used throughout the software application.

Figure 13:
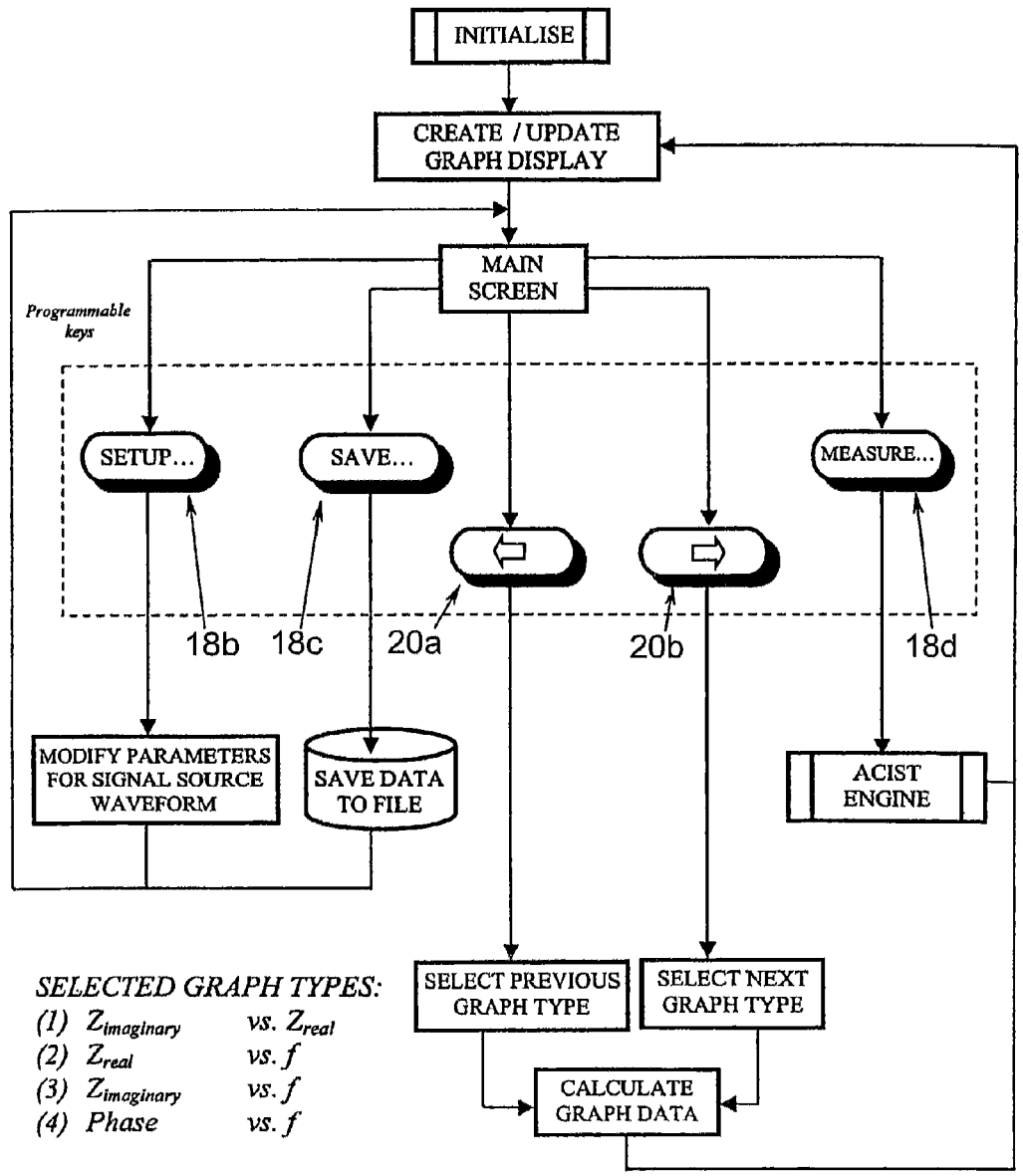
FIG. 13 a block diagram of an EIS operation achieved when an ACIST™ application is embedded within the portable device of the present invention.

The program implemented within the device 10 during the use of the ACIST Engine™ is represented by a flow diagram in FIG. 13. This flow diagram shows the EIS graph for the application process which is performed by the device 10. Having the ACIST Engine™ embedded within the device 10 means that it operates as an EIS measurement instrument, termed ACIST-hpc™ (ACIST™ hand held personal computer (PC)), and displays graphs resulting from tests performed as well as offering data storage options to allow storage of information gleaned from the measurements made. When the ACIST Engine™ application is first executed, it calls on the initialisation routine to set up the DSP driver and assign hardware channels as described previously. The programmable softkeys 18a, b, c and d are then assigned their respective operations by the application, or by the user and the appropriate display chart is constructed for display on the default display page on the LCD screen 16. Virtual buttons 91, 92, 93 and 94 are added at the bottom of the main display corresponding to a function which each softkey can execute. Each virtual button works on an event driven basis such that each softkey performs a designated operation before returning to the default, or main, display page. On pressing the SETUP button, in this case virtual button, 92, a dialogue window is displayed that allows the user to modify the amplitude, $f_0$ and $f_n$ of the generated waveform. The SAVE button, in this case virtual button 93, displays a dialogue window that gives the user an option to save the acquired impedance data to a designated filename. By pressing the left cursor 20a or right cursor 20b on the housing 19 of the device 10 the graph view is changed to a different type such as Nyquist ($Z_{imaginary}$ vs $Z_{real}$) or Bode plots, that include $Z_{imaginary}$ vs f and $Z_{real}$ vs f. The MEASURE button in this case virtual button 94 executes the ACIST Engine™ thus performing a measurement as described earlier in the text. During the measurement, amber LED 15b is lit indicating that the device 10 is waiting to collect data. The amber LED 15b is switched off and a green LED 15c is switched on for a period of, for example, 2 seconds when the acquisition is complete. At this point a fitting routine is called if required and the graph view on the main display of screen 16 is updated.

Figure 14A:
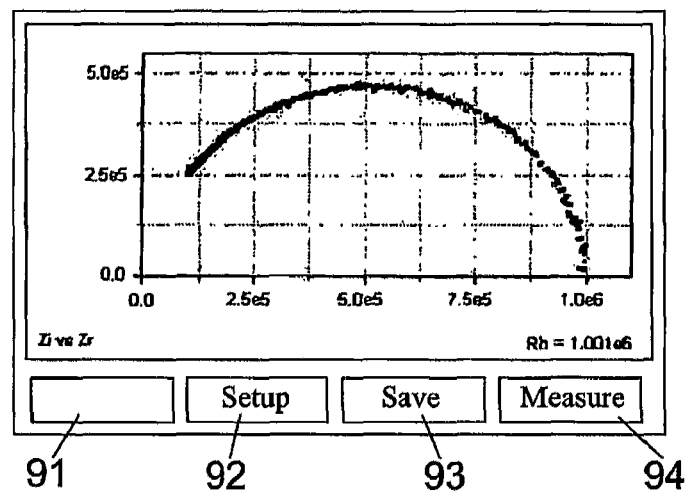
FIGS. 14a,b,c output display screens of the portable device of FIG. 2, in use.
Figure 14B:
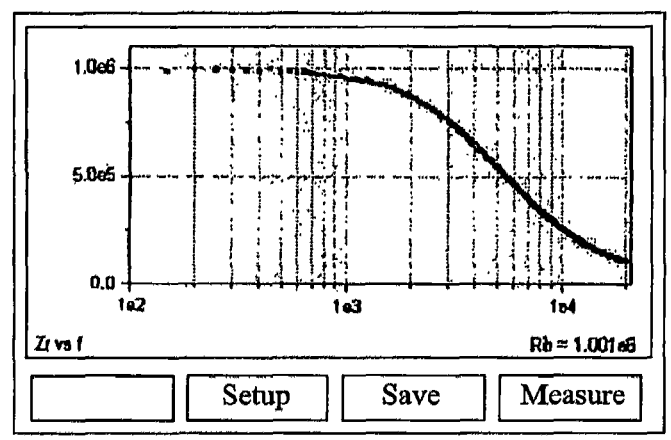
Figure 14C:
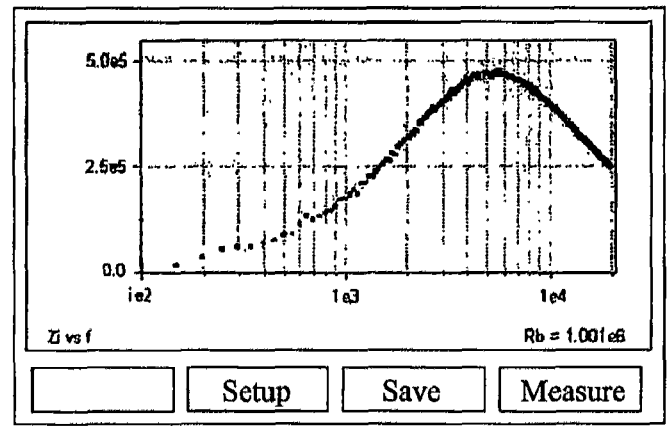

In FIGS. 14a, b and c some screen displays from the EIS application presenting the result of measuring the impedance response of a parallel RC dummy test circuit constructed from a 1MΩ resistor and a 15 pF capacitor. The source waveform was generated from the summation of 200 sinusoids, each of 15 mV amplitude and random phase, representing the frequency range 100 Hz to 20 kHz, such as that shown in FIG. 10d. The display is provided by a graphical user interface such as FIGS. 14a, b and c. In FIG. 14a there is shown a graphical representation of $-Z_{imaginary}$ vs $Z_{real}$, FIG. 14b illustrates $Z_{real}$ Vs f and in FIG. 14c there is shown $-Z_{imaginary}$ vs·f.

EXAMPLES

Some examples will now be described in order to illustrate applications of the device 10 operating as an ACIST-hpc™ in selected fields of research and development, non-destructive testing and dental and medical diagnosis. The first and second examples use the EIS program described above and relate to R&D experiments, while the third example describes a more complex system that incorporates the ACIST Engine™ being used in a dental environment. A fourth example describes use of the device 10 in a medical environment.

First Example

The first example concerns polymer electrolytes which are ionically conducting phases formed by the dissolution of salts into suitable coordinating polymers, such as polyethylene oxide (PEO). Extensive research into the development of rechargeable lithium batteries using solid polymer electrolytes is ongoing due to the advantages they offer in comparison with conventional liquid systems, for example, polymer electrolytes can be manufactured into thin films with large surface areas giving high power levels (>100 W dm$^{-3}$). Construction of all solid-state batteries can proceed in a variety of configurations, and be incorporated into devices such as notebook PC's, cellular telephones, and thin smart credit cards.

In this case the polymer electrolytes were formed by mixing and processing LiCF$_3$SO$_3$ salt and dry PEO. In this case the LiCF$_3$SO$_3$ salt was formed by trifluoromethanesulphonic acid (0.667 mol dm$^{-3}$) being slowly added to a suspension of lithium carbonate (Li$_2$CO$_3$, Aldrich) in distilled water. The solution was then stirred for 3 hours, filtered through a fine sinter and the majority of water removed on a rotary evaporator, leaving the hydrated lithium trifluoromethanesulphonate (LiCF$_3$SO$_3$) salt. The anhydrous salt is obtained after heating the hydrated salt sample under vacuum for 24 h at 150° C.

To form the polymer electrolyte, a stoichiometric mixture of LiCF$_3$SO$_3$ and dry PEO (MW=5×10$^6$), in 40EO:1Li ratio, was transferred to a stainless-steel tube for cryogrinding and a small sample of the intimate cryoground mixture was then pressed to 5 tons for 30 seconds between two stainless-steel discs in a 13 mm pellet press. This was heated for at least 3 hours at 120° C. under no applied pressure using a band heater. Upon cooling to 65° C., a pressure of 3 tons was applied and the sample allowed to cool to room temperature overnight under the applied pressure. In this case the film produced using this process was 0.36 mm thick.

Figure 15:
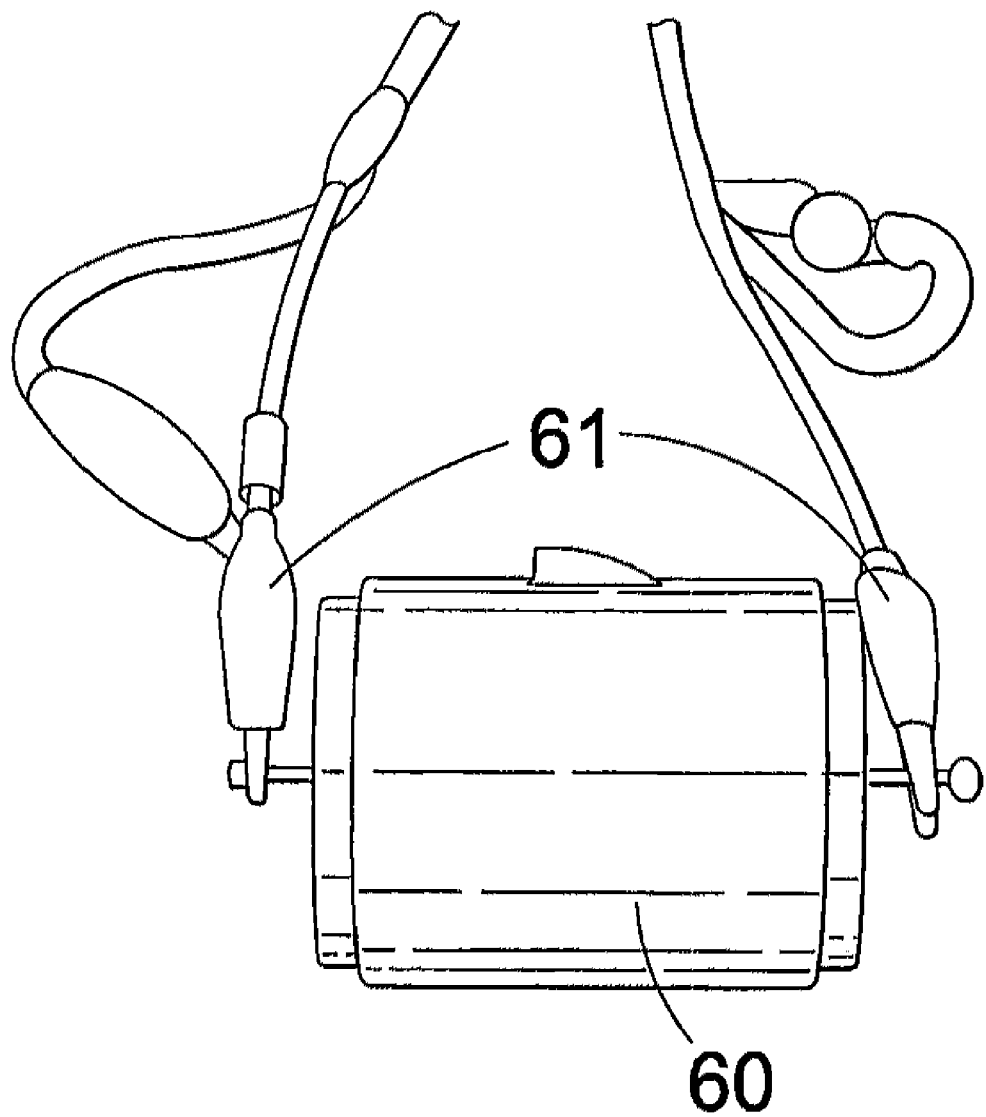
FIG. 15 a system to be tested comprising a two-electrode cell configuration.

To perform the measurements using device 10 in this example a two-electrode cell configuration 60 such as that shown in FIG. 15 was used with blocking stainless-steel electrodes which, when assembled, was placed in a Buchi oven and the temperature was monitored by a K-type thermocouple running through the cell. The geometric constant of the assembled cell was 4.734×10$^{-2}$ cm$^{-1}$. Contact between the cell 60 and the device 10 was made by BNC electrical breakthroughs from the glove box. The BNC interface 23 provides connection of the cell 60 to the ACIST-hpc™, that is device 10, via the associated cables. The cell 60 was allowed to thermally equilibrate at each temperature for at least 1 h before measurements were made.

All operations and measurements were performed in an argon filled mBraun glove box. AC measurements were made using the ACIST-hpc™ and these were compared to measurements performed by a sweeping single-sine system operating in the frequency domain. The swept-sine instrumentation in this case comprised a Solartron FRA coupled to a Solartron 1286 potentiostat, driven by a PC under custom software control.

In both cases measurements were made in the frequency range 20 kHz-100 Hz.

Figure 16A:
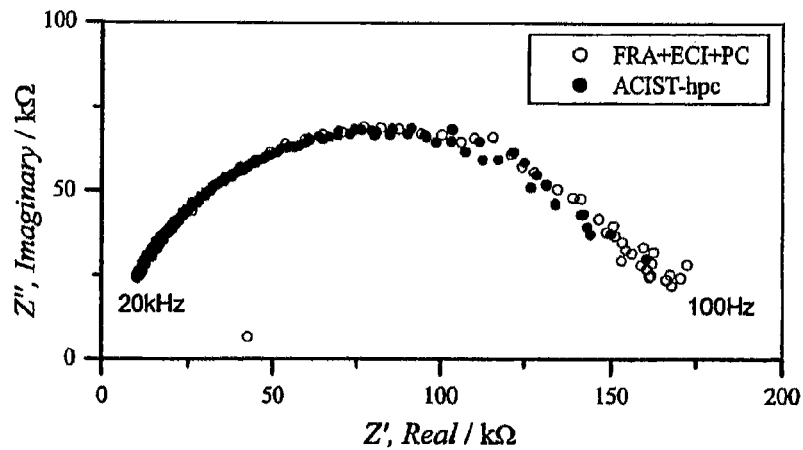
FIGS. 16a,b,c graphical representations of measurements performed on a polymer electrolyte film by a portable device of the present invention.

An idealised lithium ion conducting polymer sandwiched between symmetric blocking electrodes can be modelled by a parallel (RBCB) equivalent circuit. The resistor R$_B$ represents the migration of lithium ions moving back and forth in phase with the voltage. At the same time, a dielectric polarisation of the polymer chains occurs in the alternating field which is represented by the capacitor C$_B$. FIG. 16a shows the Nyquist plot comparison of each measurement of the polymer electrolyte film at 30° C., that is the measurements achieved using the Solartron FRA arrangement which are represented using an open circle and measurements achieved using the ACIST-hpc™ device which are shown in closed circles. As can be seen from this graph the results achieved using the ACIST-hpc™ are consistent with those achieved using conventional prior art arrangements.

Figure 16B:
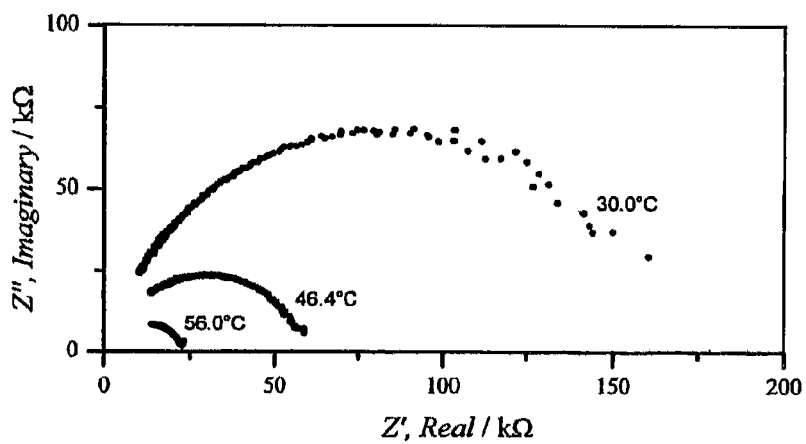

In FIG. 16b the EIS measurements achieved using the ACIST-hpc are shown for selected temperatures, in this case 30.0° C., 46.4° C. and 56.0° C.

The fitted values for R$_B$ and C$_B$ at each temperature are listed in Table 1 below along with the calculated specific conductivity a values.

TABLE 1

| Fitted values to temperature dependent EIS | | | |
|---|---|---|---|
| T/° C. | R$_B$/kΩ | σ/Scm$^{-1}$ | C/pF |
| 23.0 | 302 | 1.568 × 10$^{-7}$ | 439 |
| 30.0 | 162 | 2.922 × 10$^{-7}$ | 467 |
| 46.4 | 59.2 | 7.997 × 10$^{-7}$ | 437 |
| 56.0 | 22.6 | 2.095 × 10$^{-6}$ | 411 |

Figure 16C:
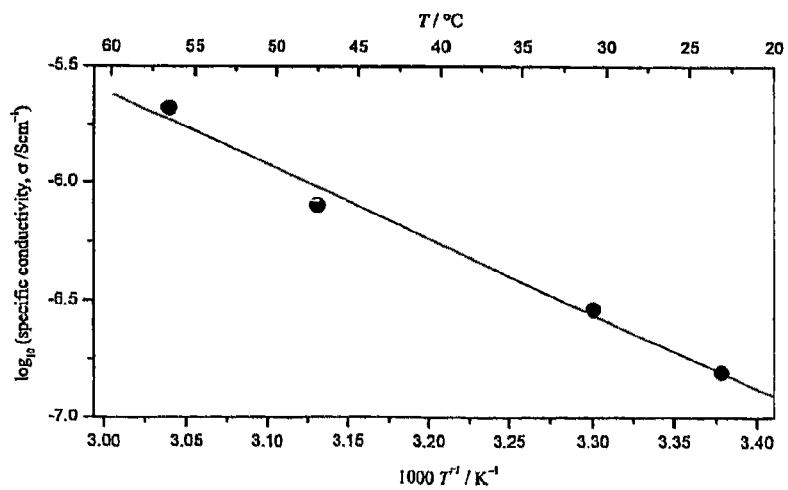

A plot of log$_{10}$σ vs. T$^{-1}$ is shown in FIG. 16c indicating that Arrhenius behaviour is observed over the chosen temperature range with an activation energy for conduction of E$_a$=60.86 kJ mol$^{-1}$.

Second Example

The second example concerns corrosion protection of engineering structures using selected coatings which are commonly used worldwide. However, degradation of such coatings does occur leading to an underlying metallic corrosion problem. In order to allow more informed decisions on which structures require attention, quantitative inspection methods have been introduced. Some DC electrochemical techniques have already been applied in the evaluation process with only limited success. EIS measurements, however, can provide a fast, non-destructive and quantitative method of assessing coating properties and identify the early onset of steel corrosion. An apparatus, incorporating device 10 using the EIS application as a basis, can operate as a field portable inspection unit to provide the user with quantitative information on coating degradation.

Figure 17A:
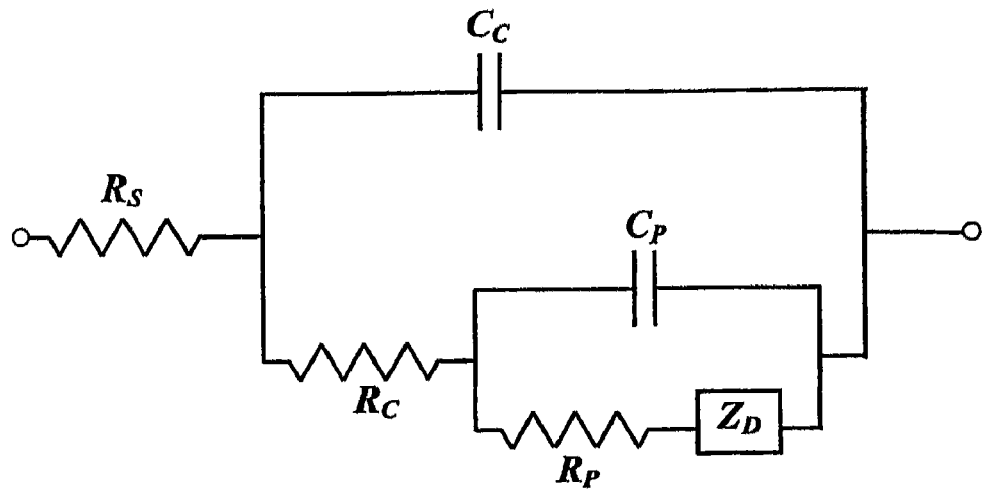
FIG. 17a a known equivalent circuit in a comparison experiment involving the portable device of the present invention.

The BNC interface 23 allows connection of an equivalent circuit model, shown in FIG. 17a, by crocodile clips 61 to the ACIST-hpc™, that is device 10, via the associated cables and using this arrangement measurements of the capacitance and/or impedance of the coating can be made to assess the thinning of the coating due to wear, or in the case of the coating being applied to provide protection the growth of the coating layer. The equivalent circuit model, proposed by Zdunek et al, representing the physical characteristics of a corrosion system, such as coated steel, is shown in FIG. 17a. R$_S$ represents the ohmic resistance of the electrolyte, while the resistance and capacitance of the coating are R$_C$ and C$_C$, respectively.

Figure 17B:
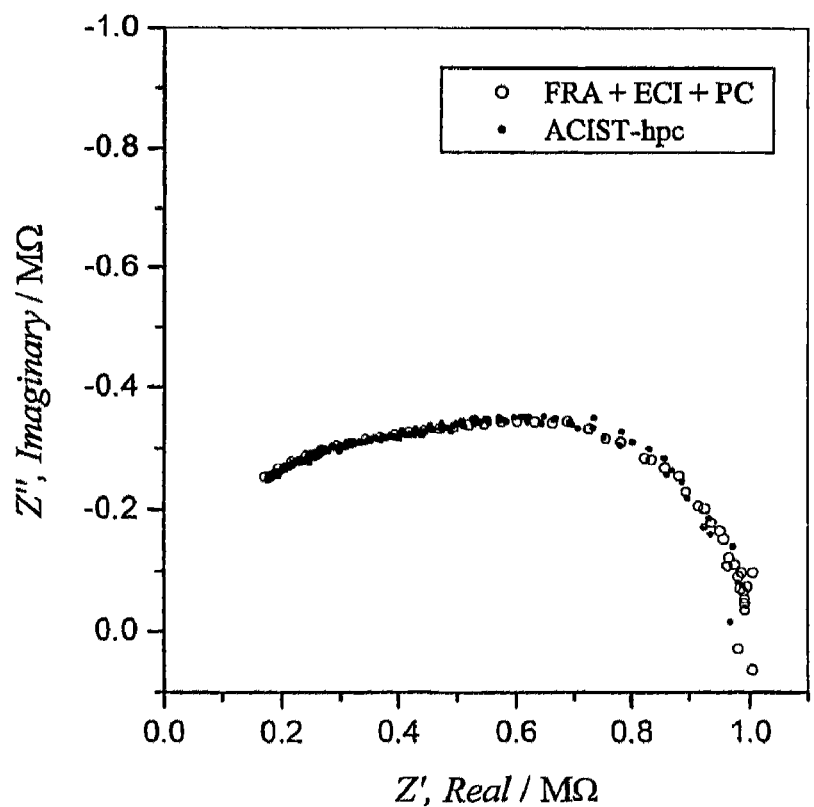
FIG. 17b a graphical comparison of measurements made using the known equivalent circuit shown in FIG. 17a and the portable device of the present invention.

The corrosion reaction is modelled by the polarisation elements R$_P$ and C$_P$. At very low frequencies an impedance response attributed to diffusion Z$_D$ may be observed. In FIG. 17b there is shown a Nyquist plot of a measurement of the equivalent circuit using the present invention in the form of ACIST-hpc™, represented on the graph using a closed circle, compared with data collected from a standard swept-sine system. The swept-sine system used with the circuit of FIG. 17a comprised a Solartron FRA coupled with a Solartron 1286 potentiostat and PC, controlled by custom data acquisition software. As can be seen from the Nyquist plot of FIG. 16b both resultant measurements are very similar, however, the time to complete the measurement run with the ACIST-hpc™ 10 was only 3 seconds compared with the 7 minutes measurement time of the large FRA-based system.

Third Example

Figure 18A:
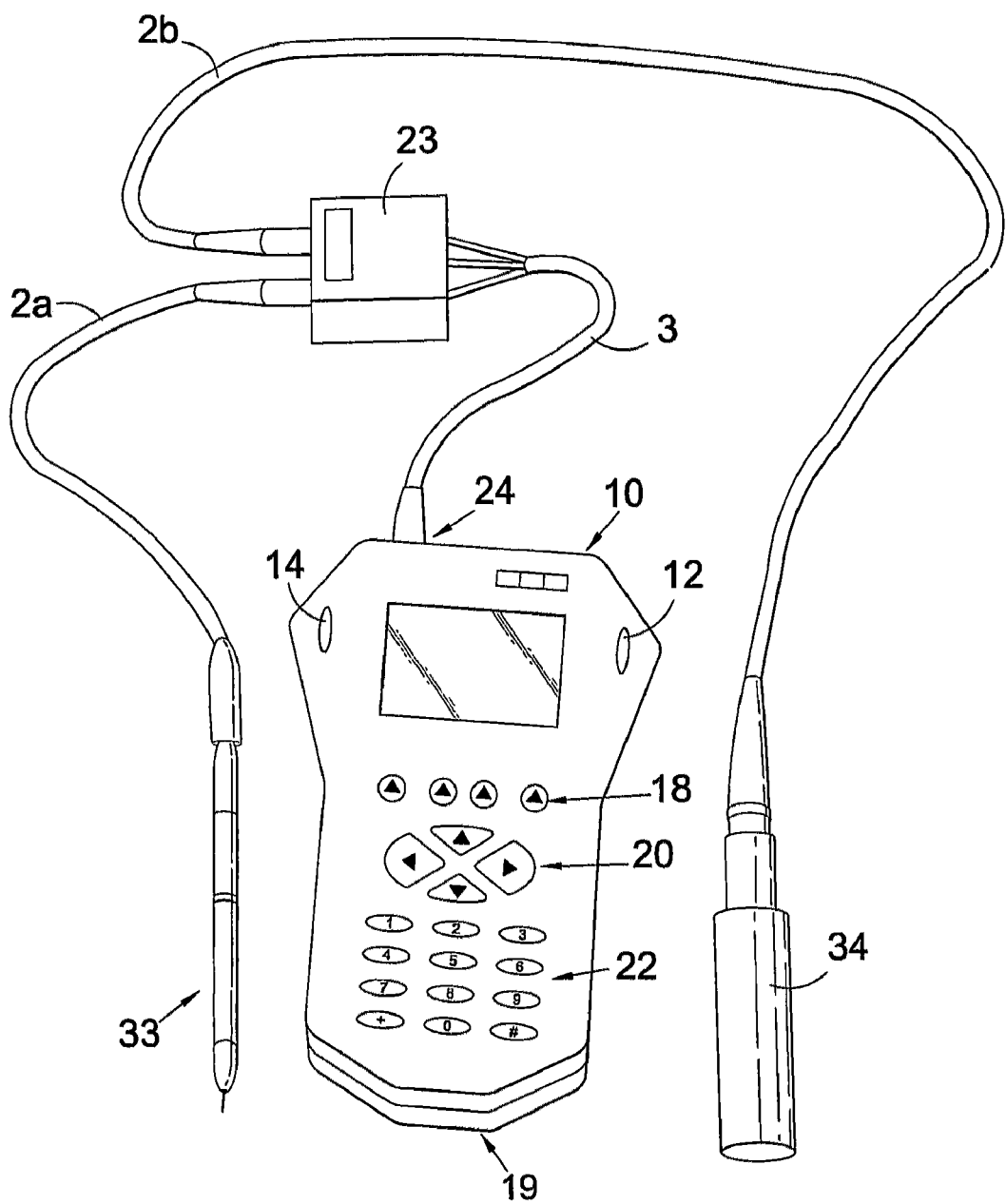
FIG. 18a a dental diagnostic instrument incorporating the portable device of FIG. 2.

As shown in FIG. 18a, the device 10 can be set up, as has been mentioned previously, for use detecting clinical, eg dental or medical conditions, having the analogue circuitry 11b for in vivo clinical examination.

It will be understood that the device 10 arranged for use detecting dental conditions as shown in FIG. 18a, may be incorporated as test equipment into or attached to the construction or structure of equipment or apparatus normally found in a dentist's surgery, eg a dentist's chair or a dentist's light unit in order to facilitate in vivo clinical examination performed by a dentist/clinician or the like. By incorporating the device 10 within the construction of a dentist's chair 100 the dentist/clinician performing the clinical examination is able to have both hands free. It will be appreciated in suggesting that the device 10 may be incorporated within a dentist's chair or light unit both the integrated incorporation and a removable arrangement in which a holding means is provided for the insertion or retention of the (hand held) device 10 of FIG. 18a is envisaged. In an alternative arrangement the casing of the device 10 may be designed to sit on a surface, eg a tabletop.

The device 10 is set up as a dental detection instrument by the addition of custom peripherals as are shown in FIG. 18a. As shown in FIG. 18b, a dental probe 33 is placed in contact with a site on a tooth to be tested and a counter electrode 34, in the form of a hand-held grip, is held by the patient. An interface such as, for example, a BNC interface box 23, the wiring of which is described in FIG. 9a, connects the probe 33 to the response channel 30 and the counter electrode to the signal source channel 31 via cables 2a and 2b respectively. The signal cable 3 leads from the interface box to the device 10.

In use, with regard to noise cancellation the two waveforms (generated X(t) and response Y(t)) are in the time domain. The "Transfer Function" is a complex (as in complex number) operation so each waveform is transformed from a function of time f(t) to a function of the complex variable s by LaPlace Transformation:

$$L\{f(s)\}=F(s)$$

where, s (the LaPlace operator)=sigma+jw,
j=imaginary number,
w (omega)=angular frequency, 2*pi*f (Hz)

Here, the single-sided LaPlace transform is used (called the Fourier Transform), i.e. damping coefficient sigma=0 so that the function is evaluated along the frequency plane and s reduces to jw.

To calculate the impedance at any frequency the transfer function G(s) is evaluated by:

$$G(s)=X(s)/(Y(s)$$

where, X(s) and Y(s) are the Fourier Transforms of X(t) and Y(t) respectively (from channels X and Y).

The DSP code in the device 10 may actually perform the operation by:

$$G=Sxy/Sxx$$

Where, Sxy (cross power spectrum)=FFT(X)·FFT(Y)/n², and Sxx (power spectrum) {|FFT(X)/n}².

Either way, in performing the transfer function after the transform of each channel essentially diminishes any overlaying pickup that is common to each channel.

As shown in FIG. 18b, it is very important that the handgrip/patient is not connected to the amplifier so that any larger amplitude noise is not amplified further. The "common mode" definition requires that the same, or at least similar, noise (frequency, phase and amplitude) is present on each input.

Figure 19:
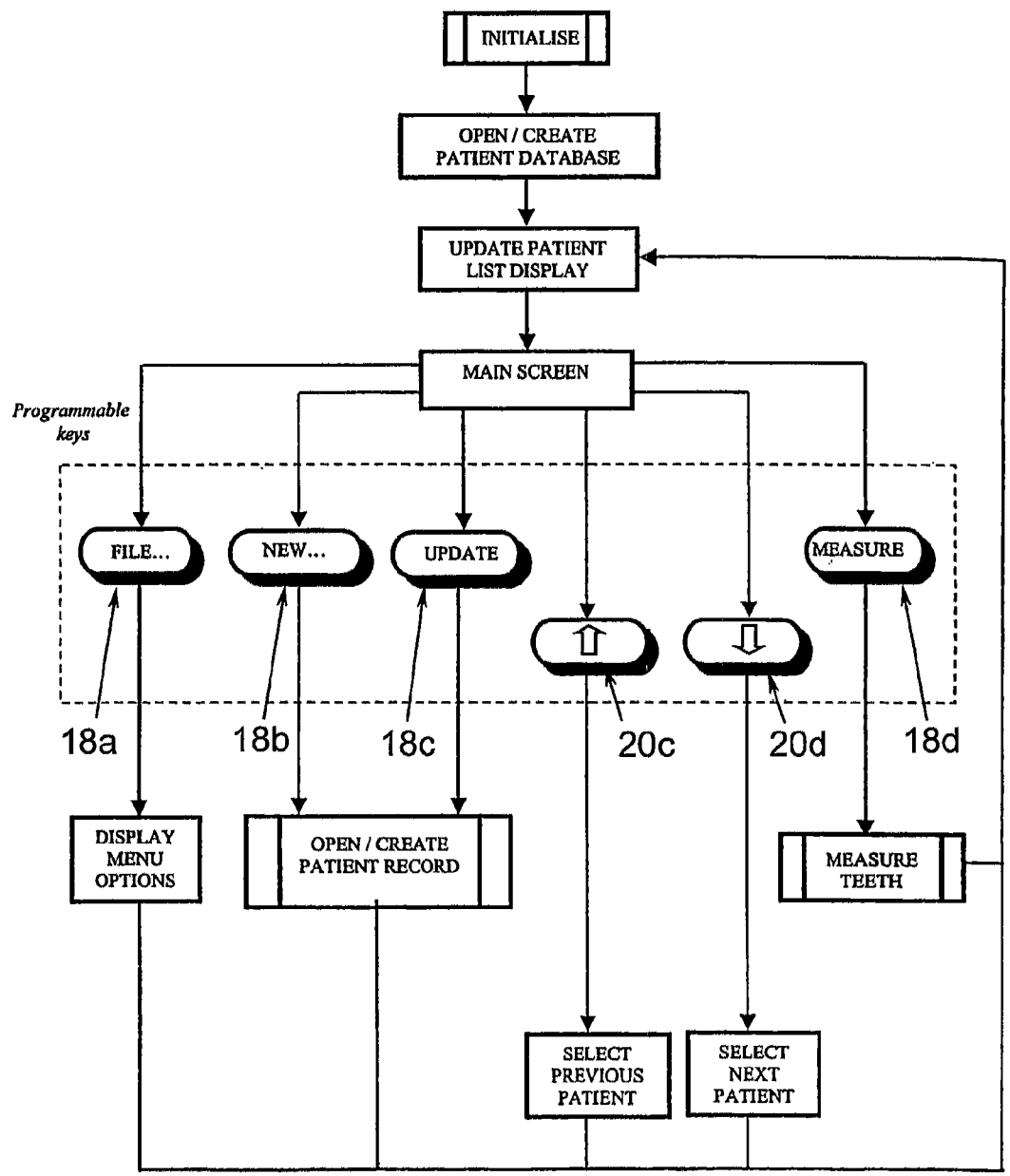
FIG. 19 a flow diagram of an example program embedded within the portable device of FIG. 2 for use in clinical applications.

In FIG. 19 there is shown a flow diagram of an example program that demonstrates use of the ACIST Engine™ in device 10 for use in the clinical field. This application, when embedded into the device 10, transforms the unit into a dental caries diagnostic tool that offers EIS measurement capability and a database of patient records. Each of the records stores personal details of the patient and results of measured teeth for each visit. The actual functionality of the measurement, including an impedance plot, is not normally shown to the user.

When the application is first executed, it calls the INITIALISE routine to set up the DSP driver and assign hardware channels. The programmable softkeys are then assigned their respective operations and the patient database if it already exists is loaded, or otherwise a new record is created. The main screen display is updateable to show a list of each patient with summary details, an example of which is shown in FIG. 20a. Virtual buttons 91, 92, 93, and 94 are added at the bottom of the main screen corresponding to each softkey function and these work on an event driven basis as detailed previously performing a designated operation before returning to the main screen. On pressing the FILE button 91 a popup menu is presented that offers the user a selection of options that may include battery status, file uploading or downloading to a PC and erase record. The NEW button 92 displays an empty patient details page for the new record, which is shown in FIG. 20b, and that prompts the user to complete the form including a unique identifier code. The softkey functions are modified in the patient details page to allow the user to access additional pages within the same patient record. These other pages include visit dates, tooth selection which shown in FIG. 20c, and table of results. The visits and results pages are only accessible from within an existing record that contains a measurement. Once the new record details have been entered, the OK button 12 is pressed to add the record to the database, or CANCEL button 14 to reject changes. The UPDATE button 93 opens the patient details page and displays the contents of the currently selected patient. The results recorded at previous visits can be viewed in a table. By pressing the up cursor 20c or down cursor 20d the selection on the main screen, is moved through the patient list. The MEASURE button 94 displays the measurement screen for the currently selected patient, as shown in FIG. 20d. Within this page, the user can select any surface of any tooth and move backwards and forwards through the selections as required as shown in FIG. 20d. The softkeys were again reprogrammed to offer appropriate functionality. The GO button 94 on the measure screen executes the ACIST™ Engine and performs the measurement upon a tooth. During the measurement, amber LED 15b is lit indicating that the instrument is waiting to collect data. The amber LED 15b is switched off and green LED 15c is switched on for 2 seconds when the acquisition is complete.

A fitting routine is then called and the measurement screen of FIG. 20d is updated with the result code before moving the selection to the next tooth or surface in the sequence. The clinician then moves the probe 33 on to the next tooth, if desired, so as to map a number, e.g. set of teeth. At any time the user can press the OK button 12 to accept the data or CANCEL button 14 to reject the measurements. On returning to the main screen of FIG. 20a, the patient list is updated to reflect the visit. The patient database can, as has been described, be uploaded to a desktop PC by serial cable, wireless iRda or by transferral of Flash data storage.

Figure 21A:
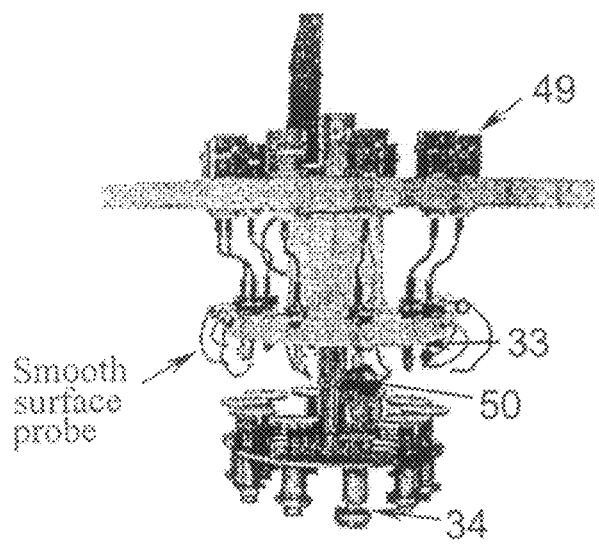
FIGS. 21a,b,c an electrode arrangement for use with the portable device of FIG. 2 when performing in vitro measurements.
Figure 21B:
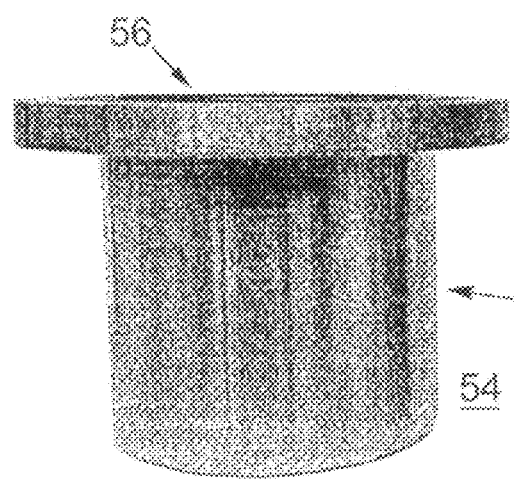
Figure 21C:
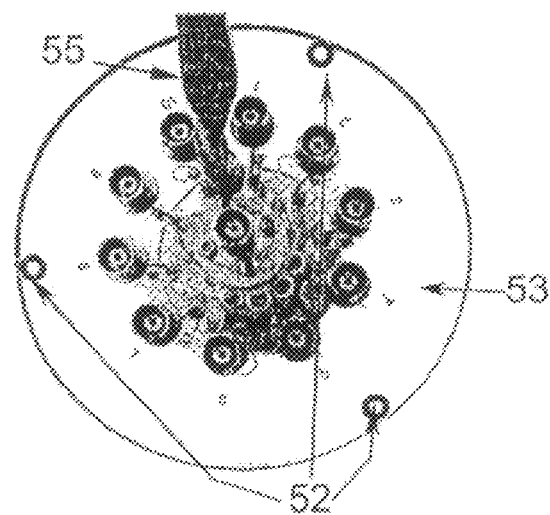

For in vitro measurements, a cell comprising of ten springloaded compartments made of stainless-steel for holding whole teeth is shown in FIGS. 21a, 21b and 21c. Each compartment has a common contact acting as a counter electrode 34. Above each tooth is a fixed stainless-steel probe that acted as a working electrode 33. To this is attached a Perspex™ lid 53 with electrical breakthroughs to BNC connections 49. After loading the teeth, or as shown in FIG. 21a, a tooth 50, on which measurements are to be performed, the assembled unit 54 is placed inside a stainless-steel can 51 filled with approximately 250 ml of 0.1 mol dm$^{-3}$ saline+thymol mixture. An O-ring 56 maintains the seal when the unit is screwed into place via the holes 52 provided on Perspex™ lid 53. A "K"-type thermocouple allows accurate monitoring of the solution temperature within the can 51. The complete can 51 is placed into an oil bath (not shown) that is thermostatically controlled by a Haake DC5 controller and cooler to within ±0.1° C. The cell is typically left to equilibrate at each temperature for approximately 40 minutes before measurements are made. AC measurements are made using the ACIST-hpc™ application detailed previously.

Figure 22A:
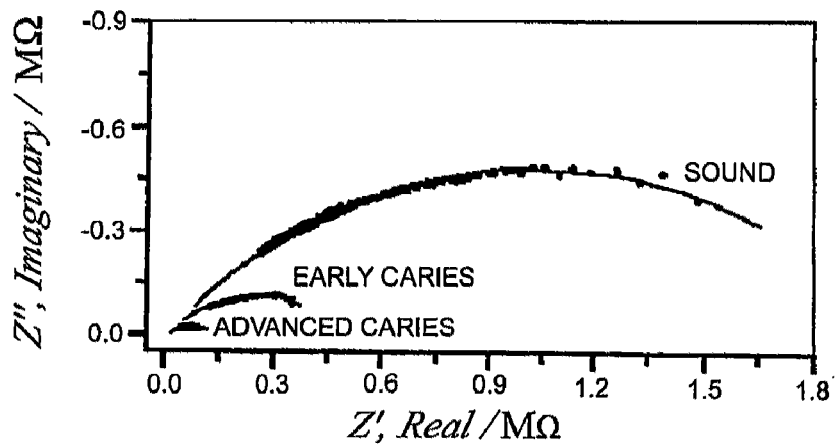
FIGS. 22a,b graphical representations of typical AC impedance spectra for whole human teeth measured using the portable device of FIG. 2.
Figure 22B:
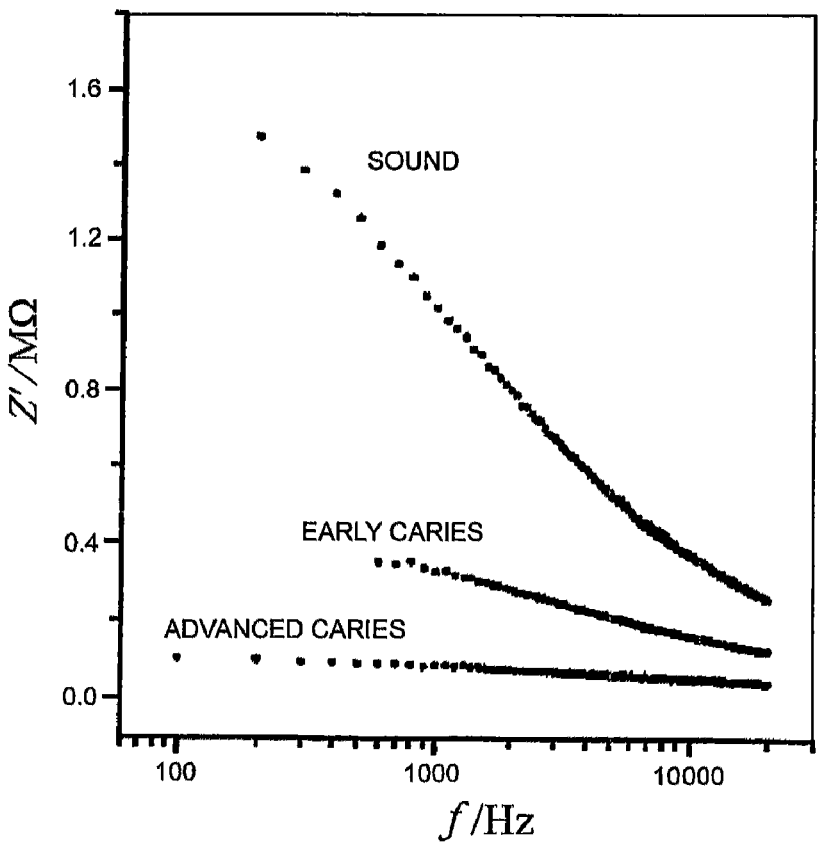

The graphs shown in FIGS. 22a and 22b present typical AC impedance spectra obtained from the occlusal surface of whole human teeth in vitro while controlled for hydration and temperature at 30° C. The effect of caries on these measurements is clearly demonstrated with the measurements having been performed on sound teeth, teeth showing advanced caries and teeth showing early caries. The impedance values for each group differ significantly from the other two groups. Impedance of a sound tooth surface approaches 2 MΩ while the presence of early caries reduces the impedance to approximately 400 kΩ. More advanced caries lowers the impedance to around 100 kΩ.

Figure 23A:
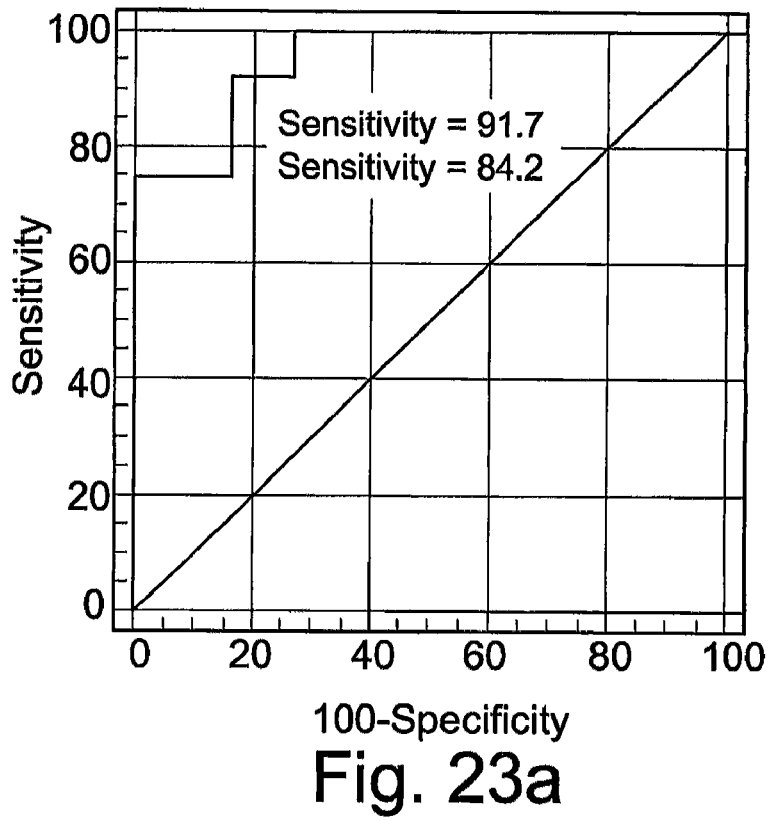
FIGS. 23a,b receiver operating characteristics for measurements made on whole teeth using the portable device of FIG. 2.
Figure 23B:
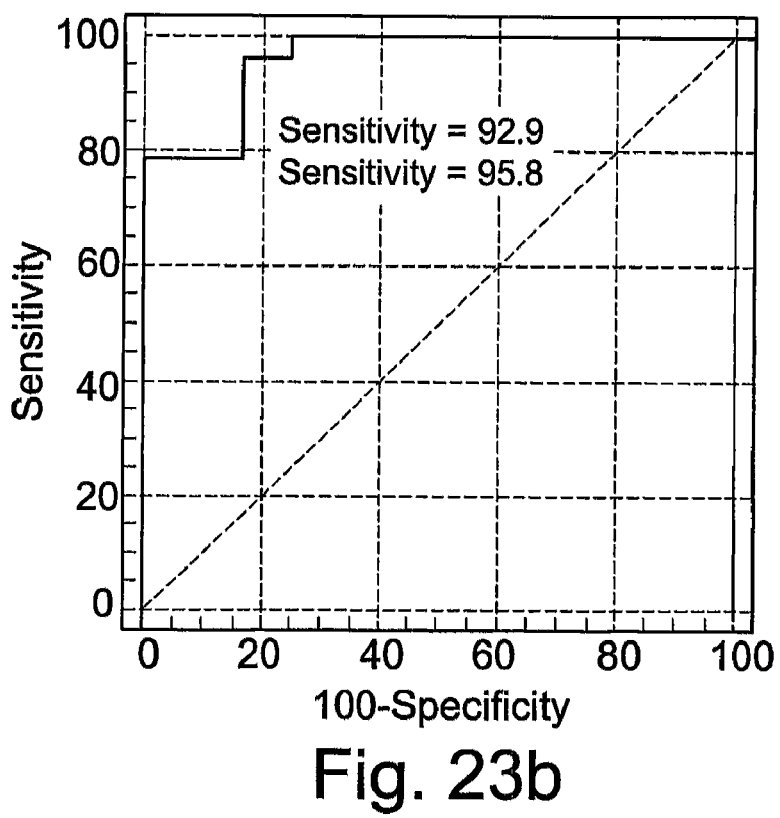

FIGS. 23a and 23b show receiver operating characteristic (ROC) curves for measurements made on whole teeth. In FIG. 23a the in vivo values for sensitivity and specificity were 91.7% and 84.2%, respectively, and in FIG. 23b the in vitro values for sensitivity and specificity were 92.9% and 95.8%, respectively. In all cases, measurements were validated by histology. These high values of sensitivity and specificity demonstrate the potential of the device of the present invention for the detection of dental caries by EIS, or ACIST™. By using in vivo probes engineered specifically for the oral environment, the successful execution of the technique in the clinic and examiner reproducibility could be improved further.

Fourth Example

An alternative arrangement, falling within the scope of the present invention, involves the device 10 being set-up for performing in-vivo clinical examinations in a medical environment.

Figure 24:
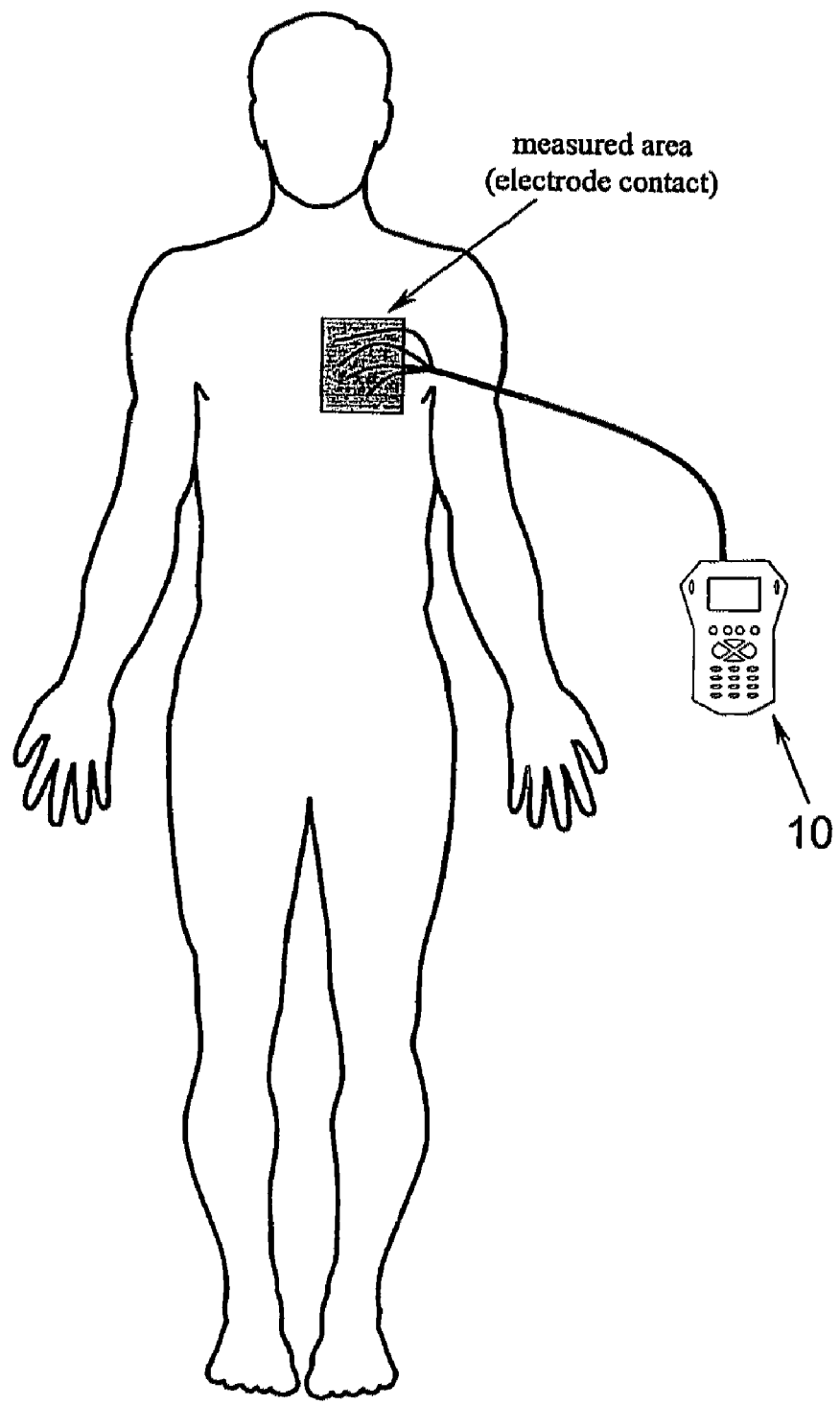
FIG. 24 an electrode arrangement associated with the portable device of FIG. 2 when used in performing analysis of skin tissue.

As is shown in FIG. 24, the device 10 is provided with an array of flat pad electrodes, with in this case, one of these electrodes being employed as the counter electrode. However, the array design can be configured in any desired custom manner. Each electrode is held against a patients skin by adhesive. The counter electrode may alternatively take the form of a hand held stick to be gripped by the patient. In the arrangement shown, the device 10 is configured for use performing measurements in the chest area carrying out, for example, skin scans in order to detect the presence of tumours, lesions, cysts or the like. However, it will be appreciated that the device may be adapted for internal tests, e.g. in humans or in veterinary use. Tests may include endoscopy, cardiology and tests for prostate conditions.

During the examination, the patient, has the flat pad electrodes attached to their skin by temporary adhesive means, in this case sticking plaster. The medic or the like performing the examination places the electrodes on the skin of the patient and performs bio-impedance measurements using the device 10.

Living tissues have differing, often unique electrical properties, so structural and chemical alterations may be reflected in impedance changes. Of importance to medicine would be the determination of pathology via the use of such non-destructive electrical methods.

The device of the present invention may be used to determine changes in tissues or cells that may be physiological, pathological or pharmacologically induced. Therefore changes such as inflammatory, infective, ischaemic, neoplastic, metabolic, fibrotic, necrotic, hypertrophic, hyperplastic or degenerative, etc may be measured. Such measurements are also useful in the evaluation of cardiovascular, pulmonary and renal function, body fat estimation, hydration, etc. All of the above may be visualised using imaging techniques such as electrical impedance tomography (EIT). The device of the present invention may also be used to distinguish normal tissue/biological material from that with any changes adverse or otherwise that may be acquired, developmental or age related, where such changes may be determined by the means of applying an electrical stimulus and measuring its response.

Figure 25:
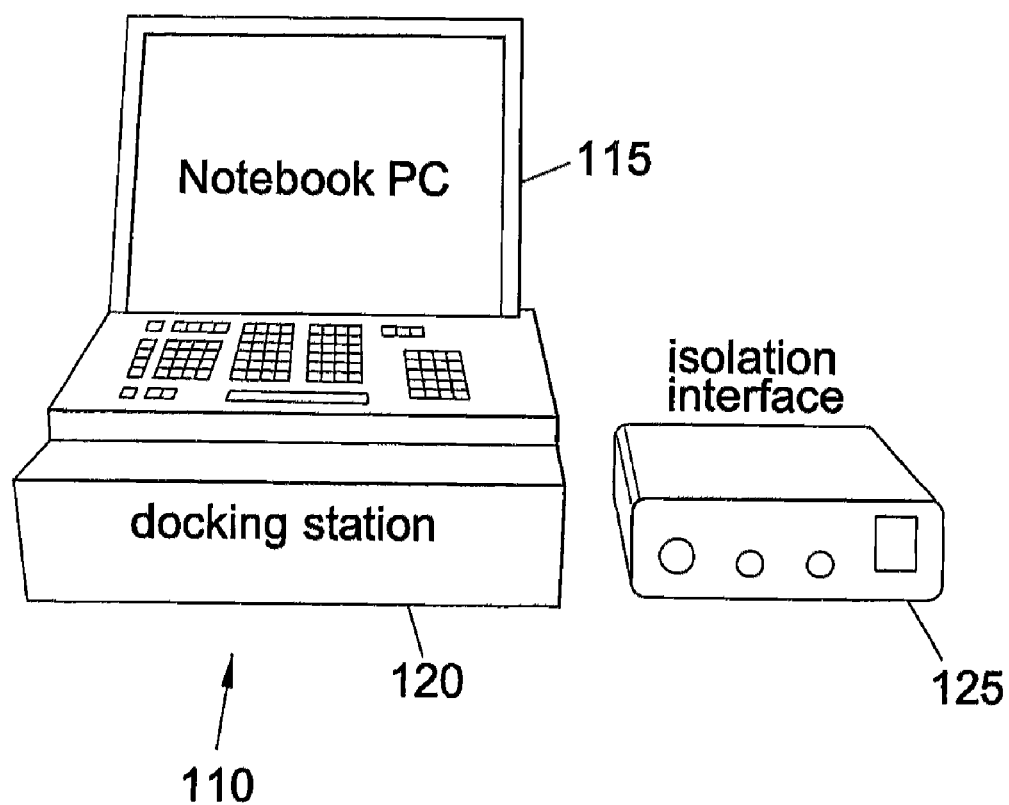
FIG. 25 a front view of a portable device according to a second embodiment of the present invention.

Referring now to FIG. 25, there is shown a test equipment, generally designated 110, according to a second embodiment of the present invention.

The test equipment 110 comprises a computer means 115 providing signal processing means and a module or docking station 120 including the signal generation means and/or the signal receiving means. In this embodiment the computer means 115 and the module 110 are separable from one another. As can be seen from FIG. 25, the test equipment 110 optionally includes an isolation unit 125 for electrically isolating a system to be tested, e.g. from a mains power supply of the module 120, and/or computer means 115, in use. This is particularly desirable if the system comprises a dental or medical system in vivo. Also in this embodiment the computer means 115 and the module 120 are docked together, eg by placing the computer means 115 on a docking station of module 120, so as to electrically interconnect each to the other. The computer means 115 can be seen in FIG. 20 to be a notebook or laptop type PC.

The test equipment 110 may in a practical realisation comprise any suitable PC or notebook PC with a module 120 (or docking station) including, eg a National Instruments PCI-4451 or 4452 Data Acquisition Card (DAC), Solartron 1296 interface (clinical or non-clinical) or other ECI (eg 1286/1287 or amplifier) for non-clinical, and software (eg based on National Instruments LABview software) customised for specific uses.

Various modifications may be made to the embodiments and arrangements hereinbefore described without departing from the scope of the invention.

For example, the signal generated by the device 10 has been described as a plurality of sine waves in a preferred mode of operation or as a simple square wave, swept sine wave, single sine wave, single DC voltage step, or square wave over one period in alternatively selectable mode of operation. However, other wave forms may be generated.

Also, in the description, the iRda port 26 has been detailed as providing a link between the device 10 and a PC for data transfer; however the iRda port 26 can alternatively be used as a link to other devices to allow wireless data transfer or printing. Similarly, recharging of the battery may be performed wirelessly if an inductive charging unit is incorporated into the device.

While the panel of the device 10 has been shown in two configurations 17a and 17b, the I/O configurations of the device can be configured in any desired custom manner, with the associated analogue circuitry 11 being correspondingly customised. For example, the amplifier gain stage with current-to-voltage conversion on response input channel 30 may be by-passed and output channel 31 to input channel 29 can be switched off, this allows an additional interface, such as a potentiostat, to be coupled to the device and allow other ranges of experiments to be performed. Furthermore switches AS1, AS2 and AS3 allow connection of the device 10 to additional external equipment such as an electrochemical interface.

Also, in a preferred embodiment of the present invention, the complex test signal output by the device comprises a multi sine signal wherein the output waveform is constructed by the summation of sinusoids, each a multiple of the lowest frequency, and in this case measurements are performed in the time domain. In this case a test signal constructed from a plurality of frequencies is applied in the time domain and this is used to generate the corresponding frequency domain representation by Fourier Transform. The computer acquires the resultant response signal emitted by a system, to which a test signal has been applied, and performs the calculations, typically using the Fast Fourier Transform (FFT) algorithm, necessary to produce AC impedance spectra from such signals.

Regarding the probes which may be used with a device according to the present invention, these may be substantially similar to the probes disclosed in WO 97/42909 (UNIVERSITY OF DUNDEE) mentioned hereinbefore, the content of which is incorporated herein by reference.

It will also be appreciated that although the first disclosed embodiment discloses a portable test device providing a hand held PC, other implementations being provided with or including suitable signal generation and receiving means fall with the ambit of the invention, e.g. suitably adapted laptop or notebook type PCs.

Finally, it will be appreciated that the preferred portable device of the present invention is advantageously of a unitary nature; in other words, all technical means are provided within a single or unitary casing or enclosure. The preferred device is self-contained with an embedded PC with signal generation/output, data acquisition/input and analysis capabilities.

The invention claimed is:

1. A portable apparatus for detecting a dental condition in dental hard tissue by applying electrical stimulus to the dental hard tissue in a dental system and acquiring response of the dental system, the apparatus comprising:
signal generation means;
signal receiving means;
signal processing means; and
electrode means which are, in use, applied to an outer surface of the dental hard tissue,
wherein a generated signal is applied to the outer surface of the dental hard tissue by said electrode means, a response signal is detected by said electrode means and received by the signal receiving means, the applied and received signals undergo processing by the signal processing means,
wherein the signal generation means and signal receiving means are configured to apply the electrical stimulus to the outer surface of the dental hard tissue having an impedance of at least 100 kOhms and wherein the signal processing means is configured to process the generated signal so as to detect a dental condition in the said dental hard tissue.

2. A portable apparatus as claimed in claim 1, wherein the signal generation means comprises a signal assembly unit that is software controllable and operates at least in one mode according to an algorithm:

$$E_k = a_o \sum_{i=1}^{n} \sin(2\pi i f_0 t_k + \theta_i)$$

where $E_k$ = voltage at any given time $t_k$,
$\theta_i$ = phase randomised for each periodic signal so as to provide the plurality of periodic output signals,
$f_o$ is a user defined fundamental lower frequency, and $a_o$ is a constant.

3. A portable apparatus as claimed in claim 1 further comprising data storage means to which the data is transferred for storage.

4. A portable apparatus as claimed in claim 1 wherein the apparatus is adapted to be hand held.

5. A portable apparatus as claimed in claim 1 wherein the apparatus includes means for visually displaying data.

6. A portable apparatus as claimed in claim 1 wherein the apparatus is adapted to measure an electrical impedance of the system.

7. A portable apparatus as claimed in claim 1 wherein the apparatus is battery operated.

8. A portable apparatus as claimed in claim 7 wherein the apparatus is connectable to a main power supply to allow charging of the battery to take place.

9. A portable apparatus as claimed in claim 1 wherein the electrode means comprise at least a first electrode and a second electrode wherein the first electrode applies the generated signal to the system to be tested and the second electrode collects a response signal from the system tested.

10. A portable apparatus as claimed in claim 9 wherein the apparatus includes means for ensuring connection to an external power supply and connection to the electrode means cannot occur simultaneously.

11. A portable apparatus as claimed in claim 9 wherein the apparatus is arranged such that connection to an external power supply and the electrode means can occur simultaneously.

12. A portable apparatus according to claim 1, wherein the electrode means comprises a hand-held counter electrode.

13. A portable apparatus as claimed in claim 1 wherein the apparatus is provided with only one input/output port and wherein the apparatus cannot be connected to an external power supply and a system to be tested simultaneously.

14. A portable apparatus as claimed in claim 1 wherein the apparatus is provided with two or more input/output ports wherein the power to the apparatus and the signals transferring to and from the apparatus are assigned to individual input/output ports.

15. A portable apparatus as claimed in claim 1 wherein the signal applied to the system comprises at least one period of a periodic signal such as an AC signal.

16. A portable apparatus as claimed in claim 1 wherein the applied signal is formed of a plurality of sine waves.

17. A portable apparatus as claimed in claim 16 wherein each of the sine waves is of a different frequency and random phase.

18. A portable apparatus as claimed in claim 1 wherein the applied signal is of a single frequency.

19. A portable apparatus as claimed in claim 1 wherein the applied signal is a sine wave.

20. A portable apparatus as claimed in claim 1 wherein the signal applied to the system is a DC signal.

21. A portable apparatus as claimed in claim 1 wherein the applied signal is a square, triangle or saw tooth wave.

22. A portable apparatus as claimed in claim 1 wherein the signal processing means performs Fast Fourier Transform spectrum analysis upon the applied signal and received signal.

23. A portable apparatus as claimed in claim 1 wherein the signal receiving means includes data acquisition means.

24. A portable apparatus as claimed in claim 1 wherein the apparatus is adapted for detecting a dental condition in vivo.

25. A portable apparatus as claimed in claim 1 wherein the apparatus is adapted for detecting a dental condition in vitro.

26. A portable apparatus as claimed in claim 1 wherein the apparatus is controlled in use by embedded PC-based control software.

27. A portable apparatus as claimed in claim 1 wherein the apparatus is adapted to perform measurements with subsequent analysis, presentation, data storage and retrieval.

28. A portable apparatus as claimed in claim 1 wherein the apparatus further comprises means for performing variable amplification on the received signal.

29. A portable apparatus as claimed in claim 1 wherein the signal processing means performs signal analysis on the generated signal and received signal.

30. A portable apparatus as claimed in claim 1 wherein the electrode means comprises an array of electrodes.

31. A portable apparatus as claimed in claim 1 further adapted to generate a signal having a frequency in the range of 1Hz-100kHz.

* * * * *